United States Patent
Widman et al.

(10) Patent No.: US 11,912,800 B2
(45) Date of Patent: *Feb. 27, 2024

(54) AMIDE-FUNCTIONALIZED POLYMERIZATION INITIATORS AND THEIR USE IN THE MANUFACTURE OF OPHTHALMIC LENSES

(71) Applicant: Johnson & Johnson Vision Care, Inc., Jacksonville, FL (US)

(72) Inventors: Michael F. Widman, Jacksonville, FL (US); Ghulam Maharvi, Jacksonville, FL (US); Shivkumar Mahadevan, Jacksonville, FL (US); Azaam Alli, Jacksonville, FL (US); Alexander Guzman, Jacksonville, FL (US); Xin Wei, Irvine, CA (US); Minghan Chen, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/821,315

(22) Filed: Aug. 22, 2022

(65) Prior Publication Data

US 2023/0105992 A1 Apr. 6, 2023

Related U.S. Application Data

(60) Provisional application No. 63/249,646, filed on Sep. 29, 2021.

(51) Int. Cl.
*C08F 22/38* (2006.01)
*A61K 9/00* (2006.01)
*A61K 31/785* (2006.01)

(52) U.S. Cl.
CPC ............ *C08F 22/38* (2013.01); *A61K 9/0048* (2013.01); *A61K 31/785* (2013.01)

(58) Field of Classification Search
CPC ...... C08F 22/38; A61K 31/785; A61K 9/0048
See application file for complete search history.

(56) References Cited

U.S. PATENT DOCUMENTS

| | | | |
|---|---|---|---|
| 3,408,429 A | 10/1968 | Otto | |
| 3,660,545 A | 5/1972 | Wichterle | |
| 3,808,178 A | 4/1974 | Gaylord | |
| 4,018,853 A | 4/1977 | Le et al. | |
| 4,113,224 A | 9/1978 | Clark et al. | |
| 4,120,570 A | 10/1978 | Gaylord | |
| 4,136,250 A | 1/1979 | Mueller et al. | |
| 4,153,641 A | 5/1979 | Deichert et al. | |
| 4,190,277 A | 2/1980 | England | |
| 4,197,266 A | 4/1980 | Clark et al. | |
| 4,620,954 A | 11/1986 | Singer et al. | |
| 4,680,336 A | 7/1987 | Larsen et al. | |
| 4,740,533 A | 4/1988 | Su et al. | |
| 4,892,402 A | 1/1990 | Sawamoto et al. | |
| 4,910,277 A | 3/1990 | Bambury et al. | |
| 5,034,461 A | 7/1991 | Lai et al. | |
| 5,039,459 A | 8/1991 | Kindt-larsen et al. | |
| 5,070,215 A | 12/1991 | Bambury et al. | |
| 5,244,981 A | 9/1993 | Seidner et al. | |
| 5,258,024 A | 11/1993 | Chavel et al. | |
| 5,310,779 A | 5/1994 | Lai | |
| 5,314,960 A | 5/1994 | Spinelli et al. | |
| 5,321,108 A | 6/1994 | Kunzler et al. | |
| 5,331,067 A | 7/1994 | Seidner et al. | |
| 5,371,147 A | 12/1994 | Spinelli et al. | |
| 5,387,662 A | 2/1995 | Kunzler et al. | |
| 5,539,016 A | 7/1996 | Kunzler et al. | |
| 5,726,733 A | 3/1998 | Lai et al. | |
| 5,849,811 A | 12/1998 | Nicolson et al. | |
| 5,944,853 A | 8/1999 | Molock et al. | |

(Continued)

FOREIGN PATENT DOCUMENTS

| | | |
|---|---|---|
| CN | 1723411 A | 1/2006 |
| CN | 102405239 A | 4/2012 |
| CN | 105837731 A | 8/2016 |
| EP | 0080539 B1 | 6/1983 |
| EP | 0632329 A1 | 1/1995 |
| EP | 1286823 B1 | 6/2009 |
| EP | 2265430 B1 | 10/2011 |
| EP | 3598181 B1 | 1/2020 |
| JP | 2003512513 A | 4/2003 |
| JP | 2017524566 A | 8/2017 |
| RU | 1789208 A1 | 1/1993 |
| RU | 2334770 C1 | 9/2008 |

OTHER PUBLICATIONS

Luigi Angiolini, et al., Polymeric Systems Bearing Side-Chain 2,6-Dimethylbenzoyldiphenyl phosphinoxide Moieties for UV Curable Coatings; Synthesis and Photoinitiation Activity, 57 J App. Poly. Sci. 519 (Year: 1995).*

(Continued)

*Primary Examiner* — Sean M Basquill
(74) *Attorney, Agent, or Firm* — Raef M. Shaltout

(57) ABSTRACT

Provided are compounds that may function as functionalized polymerization initiators, for instance in the manufacture of ophthalmic lenses, and to methods of such manufacture. The compounds are of formula I:

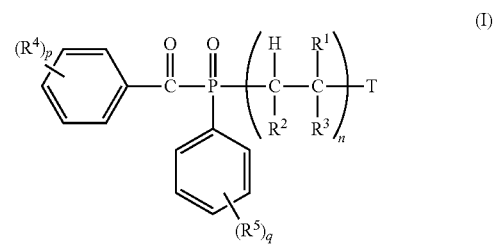

wherein $R^1$, $R^2$, $R^3$, $R^4$, $R^5$, T, p, q, and n are as defined herein.

18 Claims, 9 Drawing Sheets

(56) References Cited

U.S. PATENT DOCUMENTS

| | | | |
|---|---|---|---|
| 5,962,548 A | 10/1999 | Vanderlaan et al. |
| 5,965,631 A | 10/1999 | Nicolson et al. |
| 5,998,498 A | 12/1999 | Vanderlaan et al. |
| 6,020,445 A | 2/2000 | Vanderlaan et al. |
| 5,760,100 A | 11/2000 | Nicolson et al. |
| 6,367,929 B1 | 4/2002 | Maiden et al. |
| 6,372,815 B1 | 4/2002 | Sulc et al. |
| 6,586,038 B1 | 7/2003 | Chabrecek |
| 6,617,373 B2 | 9/2003 | Sulc et al. |
| 6,822,016 B2 | 11/2004 | Mccabe et al. |
| 6,867,245 B2 | 3/2005 | Iwata et al. |
| 6,943,203 B2 | 9/2005 | Vanderlaan et al. |
| 6,951,894 B1 | 10/2005 | Nicolson et al. |
| 6,992,118 B2 | 1/2006 | Sulc et al. |
| 7,052,131 B2 | 5/2006 | Mccabe et al. |
| 7,119,210 B2 | 10/2006 | Schlueter |
| 7,247,692 B2 | 7/2007 | Laredo |
| 7,262,232 B2 | 8/2007 | Sulc et al. |
| 7,396,890 B2 | 7/2008 | Zanini et al. |
| 7,396,942 B2 | 7/2008 | Schuleter |
| 7,461,937 B2 | 12/2008 | Steffen et al. |
| 7,468,398 B2 | 12/2008 | Nicolson et al. |
| 7,538,146 B2 | 5/2009 | Nicolson et al. |
| 7,553,880 B2 | 6/2009 | Nicolson et al. |
| 7,572,841 B2 | 8/2009 | Chen et al. |
| 7,649,027 B2 | 1/2010 | Imai |
| 7,666,921 B2 | 2/2010 | Mccabe et al. |
| 7,691,916 B2 | 4/2010 | Mccabe et al. |
| 7,709,652 B2 | 5/2010 | Schlueter |
| 7,786,185 B2 | 8/2010 | Rathore et al. |
| 7,825,170 B2 | 11/2010 | Steffen et al. |
| 7,905,594 B2 | 3/2011 | Widman et al. |
| 7,915,323 B2 | 3/2011 | Awasthi et al. |
| 7,994,356 B2 | 8/2011 | Awasthi et al. |
| 8,022,158 B2 | 9/2011 | Rathore et al. |
| 8,119,830 B2 | 2/2012 | Schlueter |
| 8,157,373 B2 | 4/2012 | Widman et al. |
| 8,163,206 B2 | 4/2012 | Chang et al. |
| 8,240,849 B2 | 8/2012 | Widman et al. |
| 8,273,802 B2 | 9/2012 | Laredo et al. |
| 8,313,828 B2 | 11/2012 | Widman et al. |
| 8,317,505 B2 | 11/2012 | Widman et al. |
| 8,318,055 B2 | 11/2012 | Widman et al. |
| 8,399,538 B2 | 3/2013 | Steffen et al. |
| 8,415,404 B2 | 4/2013 | Nicolson et al. |
| 8,415,405 B2 | 4/2013 | Maggio et al. |
| 8,420,711 B2 | 4/2013 | Awasthi et al. |
| 8,431,669 B2 | 4/2013 | Mccabe et al. |
| 8,450,387 B2 | 5/2013 | Mccabe et al. |
| 8,454,862 B2 | 6/2013 | Andino et al. |
| 8,480,227 B2 | 7/2013 | Qiu et al. |
| 8,487,058 B2 | 7/2013 | Liu et al. |
| 8,568,626 B2 | 10/2013 | Nicolson et al. |
| 8,795,558 B2 | 8/2014 | Widman et al. |
| 8,883,872 B2 | 11/2014 | Gruützmacher et al. |
| 8,937,110 B2 | 1/2015 | Alli et al. |
| 8,937,111 B2 | 1/2015 | Alli et al. |
| 8,940,812 B2 | 1/2015 | Reboul et al. |
| 8,980,972 B2 | 3/2015 | Driver |
| 9,056,878 B2 | 6/2015 | Fujisawa et al. |
| 9,075,186 B2 | 7/2015 | Widman et al. |
| 9,125,808 B2 | 9/2015 | Alli et al. |
| 9,140,825 B2 | 9/2015 | Alli et al. |
| 9,156,934 B2 | 10/2015 | Alli et al. |
| 9,170,349 B2 | 10/2015 | Mahadevan et al. |
| 9,180,633 B2 | 11/2015 | Widman et al. |
| 9,180,634 B2 | 11/2015 | Widman et al. |
| 9,217,813 B2 | 12/2015 | Liu et al. |
| 9,244,196 B2 | 1/2016 | Scales et al. |
| 9,244,197 B2 | 1/2016 | Alli et al. |
| 9,260,544 B2 | 2/2016 | Rathore et al. |
| 9,297,928 B2 | 3/2016 | Molock et al. |
| 9,297,929 B2 | 3/2016 | Scales et al. |
| 9,417,464 B2 | 8/2016 | Wildsmith et al. |
| 9,610,742 B2 | 4/2017 | Widman |
| 9,857,607 B2 | 1/2018 | Widman et al. |
| 9,927,633 B2 | 3/2018 | Franklin et al. |
| 11,034,789 B2 | 6/2021 | Aitken et al. |
| 2002/0016383 A1 | 2/2002 | Iwata et al. |
| 2003/0125498 A1 | 7/2003 | Mccabe et al. |
| 2003/0162862 A1 | 8/2003 | Mccabe et al. |
| 2006/0142410 A1 | 6/2006 | Baba |
| 2010/0120939 A1 | 5/2010 | Phelan |
| 2012/0142805 A1 | 6/2012 | Grutzmacher et al. |
| 2013/0168617 A1 | 7/2013 | Alli et al. |
| 2013/0172440 A1 | 7/2013 | Alli et al. |
| 2013/0176529 A1 | 7/2013 | Li et al. |
| 2013/0217620 A1 | 8/2013 | Alli et al. |
| 2013/0341811 A1 | 12/2013 | Alli |
| 2014/0024791 A1 | 1/2014 | Alli et al. |
| 2014/0031447 A1 | 1/2014 | Alli et al. |
| 2014/0179824 A1* | 6/2014 | Nunez ............... G02C 7/04 |
| | | | 523/107 |
| 2015/0025169 A1 | 1/2015 | Grutzmacher et al. |
| 2015/0094395 A1 | 4/2015 | Alli et al. |
| 2015/0146159 A1 | 5/2015 | Archer et al. |
| 2018/0037690 A1 | 2/2018 | Aitken et al. |
| 2018/0052335 A1 | 2/2018 | Chen |
| 2018/0141293 A1 | 5/2018 | Bothe |
| 2018/0362558 A1* | 12/2018 | Yokoi ............... C08F 2/48 |
| 2023/0105465 A1 | 4/2023 | Widman et al. |
| 2023/0176251 A1* | 6/2023 | Widman ............ G02B 1/043 |
| | | | 351/159.24 |

FOREIGN PATENT DOCUMENTS

| | | | |
|---|---|---|---|
| SU | 1085986 A1 | 4/1984 |
| SU | 1500316 A1 | 8/1989 |
| TW | 200535156 A | 11/2005 |
| WO | 96/31792 A1 | 10/1996 |
| WO | 1999029750 A1 | 6/1999 |
| WO | 2000002937 A1 | 1/2000 |
| WO | 2000055212 A1 | 9/2000 |
| WO | 2000055214 A1 | 9/2000 |
| WO | 2001030512 A2 | 5/2001 |
| WO | 2001078971 A1 | 10/2001 |
| WO | 2003/022322 A2 | 3/2003 |
| WO | 2003022321 A2 | 3/2003 |
| WO | 2004063795 A1 | 7/2004 |
| WO | 2008003601 A1 | 1/2008 |
| WO | 2009026659 A1 | 3/2009 |
| WO | 2010121387 A1 | 10/2010 |
| WO | 2011003772 A1 | 1/2011 |
| WO | 2011034801 A1 | 3/2011 |
| WO | 2013096597 A1 | 6/2013 |
| WO | 2015038577 A1 | 3/2015 |
| WO | 2015038940 A1 | 3/2015 |
| WO | 2015200173 A1 | 12/2015 |
| WO | 2016100457 A1 | 6/2016 |
| WO | 2018026822 A1 | 2/2018 |
| WO | 2020003022 A1 | 1/2020 |
| WO | 2020065430 A1 | 4/2020 |

OTHER PUBLICATIONS

Corrales et al, Free radical macrophotoinitiators: an overview on recent advances, Journal of Photochemistry and Photobiology A: Chemistry, vol. 159 (2003), pp. 103-114.

Crivello, et al., "Photoinitiators for Free Radical Cationic & Anionic Photopolymerisation", In 2nd Edition, vol. III, pp. 275-298, 1998.

De Groot et al, Hydrophilic Polymeric Acylphospine Oxide Photoinitiators/Crosslinkers for in Vivo Blue-Light Photopolymerization, Biomacromolecules, 2001, vol. 2, pp. 1271-1278.

Engel et al, An Aliphatic Bifunctional Free Radical Initiator. Synthese of a Block Copolymer froman Azoperester by Sequential Thermal and Photochemical Initiation, Macromolecules 2003, vol. 36, pp. 3821-3825.

Georgina Muller et al, Simple One-Pot Syntheses of Water-Soluble Bis(acyl)phosphane Oxide Phtoinitiators and Their Application in Surfactant-Free Emulsion Polymerization, Macromolecular Rapid Communications, 2015, pp. 553-557, vol. 36.

(56) References Cited

OTHER PUBLICATIONS

Gunersel et al, Bisacylphosphine Oxides as bifunctional Photoinitiators for block copolymer synthesis, Die Angewandte Makromolekulare Chemie, vol. 264 Nr. 4604, (1999), pp. 88-91.
International Preliminary Report on Patentability, dated Aug. 4, 2020, for PCT Int'l Appln. No. PCT/IB2019/050427.
International Preliminary Report on Patentability, dated Aug. 4, 2020, for PCT Int'l Appln. No. PCT/IB2019/050428.
International Preliminary Report on Patentability, dated Feb. 5, 2019, for PCT Int'l Appln. No. PCT/US2017/044912.
International Search Report, dated Oct. 30, 2017, for PCT Int'l Appln. No. PCT/US2017/044912.
International Search Report, dated Jan. 20, 2023, for PCT Int'l Appln. No. PCT/IB2022/058728.
International Search Report, dated Jan. 3, 2023, for PCT Int'l Appln. No. PCT/IB2022/058726.
International Search Report, dated Jul. 17, 2019, for PCT Int'l Appln. No. PCT/IB2019/050427.
International Search Report, dated Jul. 17, 2019, for PCT Int'l Appln. No. PCT/IB2019/050428.
ISO 18369-4:2006: Ophthalmic optics—Contact lenses—Part 4: Physicochemical properties of contact lens materials.
ISO 9913-1: 1996: Optics and optical instruments—Contact Lenses—Part 1: Determination of oxygen permeability and transmissibility by the FATT method.
Jockusch et al, A Steady-State and Picosecond Pump-Probe Investigation of the Photophysics of an Acyl and a Bis (acyl)phosphine Oxide, J. Am. Chem. Soc., vol. 119, No. 47, 1997, pp. 11495-11501.
Jockusch et al, Phosphinoyl Radicals: Structure and Reactivity. A Laser Flash Photolysis and Time-Resolved ESR Investigation, J. Am. Chem. Soc., vol. 120, No. 45, 1998, pp. 11773-11777.
John E. Grievenkamp, Field Guide to Geometrical Optics, SPIE Field Guide to Geometrical Optics, 2004, 1-111, I, SPIE —The International Society for Optical Engineering, Bellingham, WA.
Kolczak, et al, "Reaction Mechanism of Moacyl- and Bisacylphosphine Oxide Photoinitiators Studied by 31P-, 13C-, and 1H-CIDNP and ESR" in J. Am. Chem. Soc., 1996, 118, pp. 6477-6489.
Sitzmann, Critical photoinitiators for UV-LED Curing: Enabling 3D Printing, Inks and Coatings, BASF, Redondo Beach, CA, Mar. 10, 2015.
Waters et al, Structure and Mechanism of Strength Enhancement in Interpenetrating Polymer Network Hydrogels, Macromolecules 2011, vol. 44, pp. 5776-5787.
International Search Report, dated Feb. 7, 2023, for PCT Int'l Appln. No. PCT/IB2022/058727.

\* cited by examiner

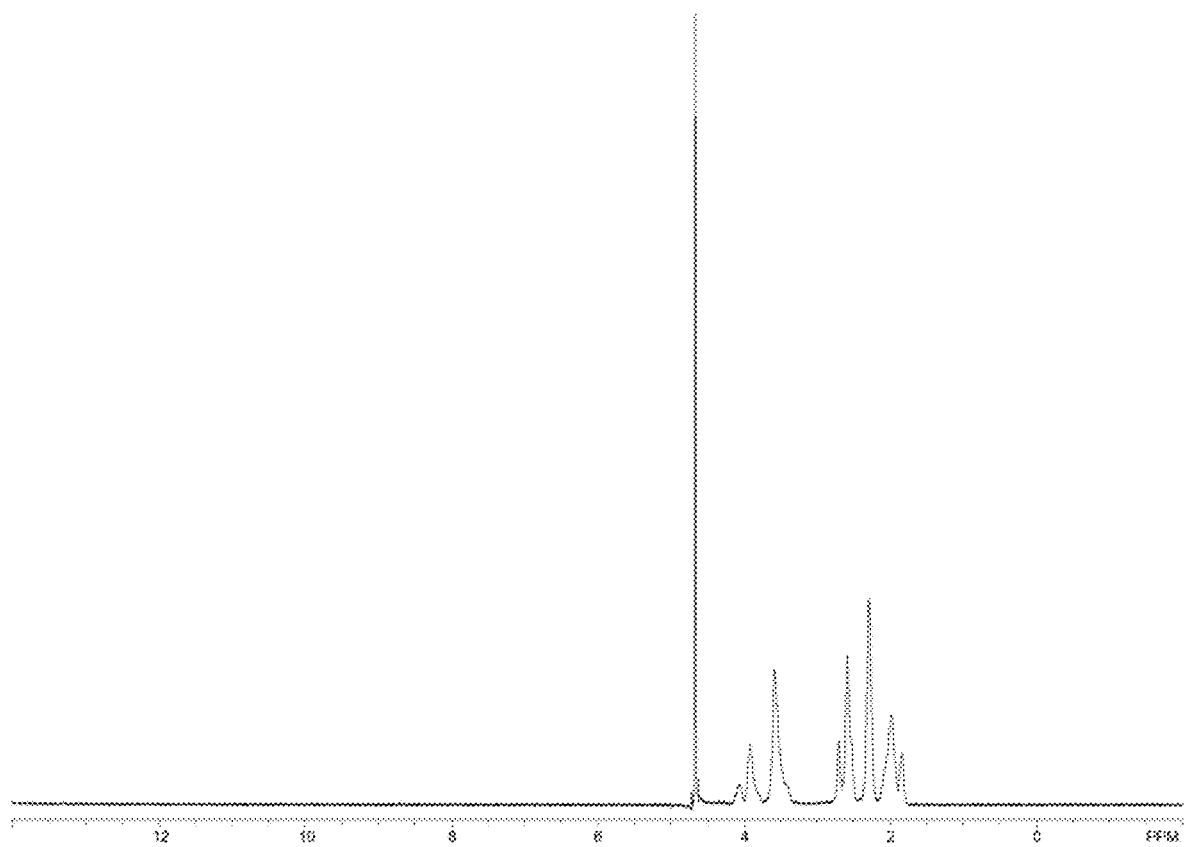
FIG. 4 - 500 MHz $^1$H-NMR spectrum of MAPO-PVP in deuterium oxide

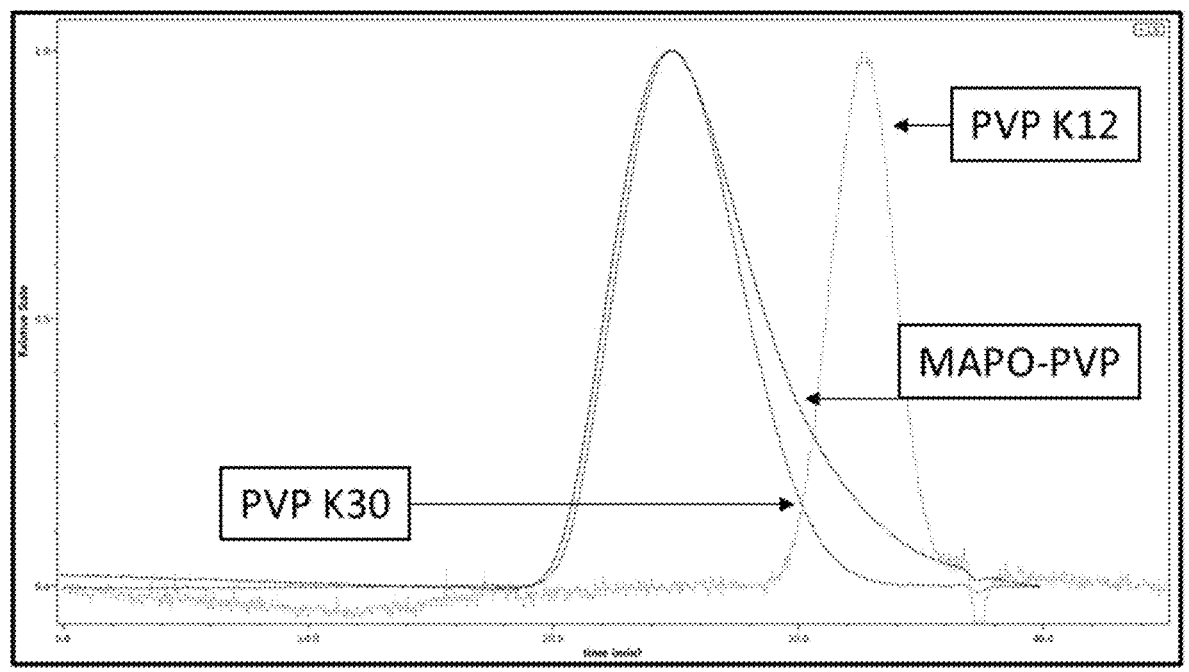
FIG. 5 – SEC-MALS Chromatograms

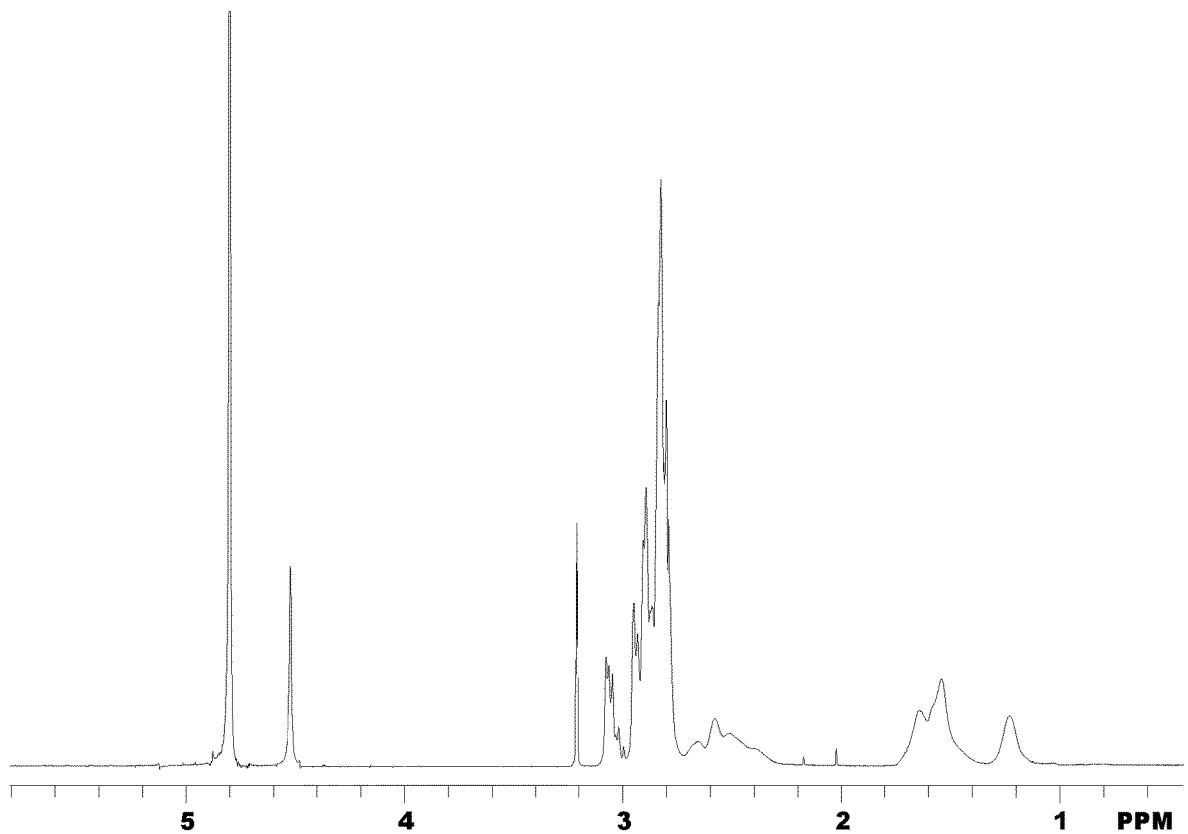
FIG. 6 - 500 MHz $^1$H-NMR spectrum of MAPO-PDMA in deuterated methanol

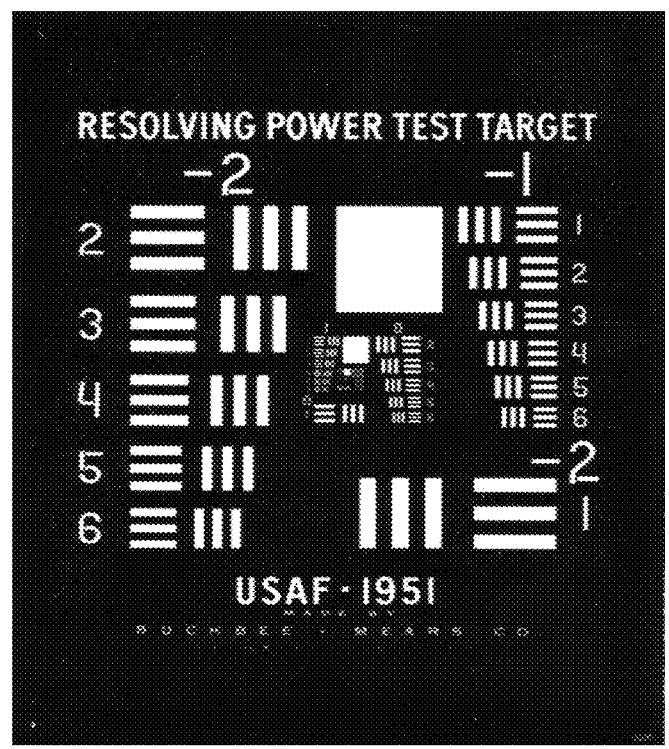
FIG. 7 - USAF 1951 Test Chart

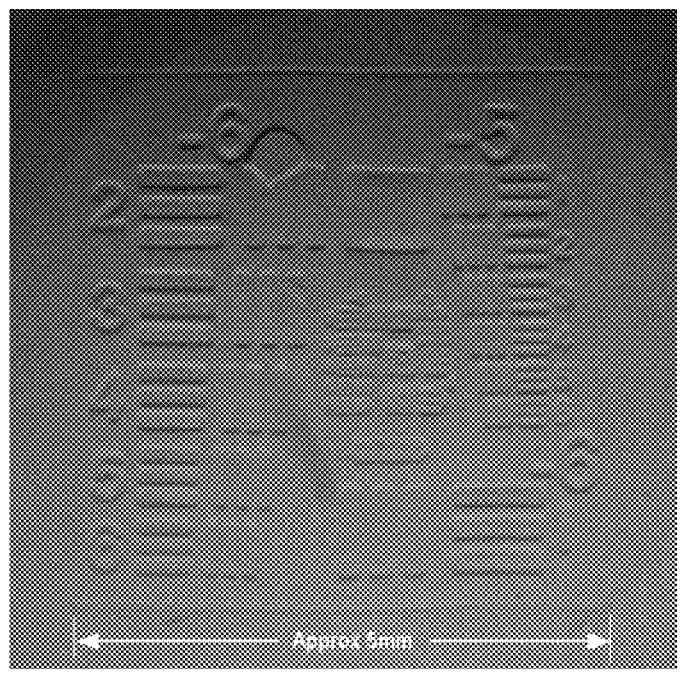
FIG. 8 - USAF 1951 Test Chart Image on the contact lens

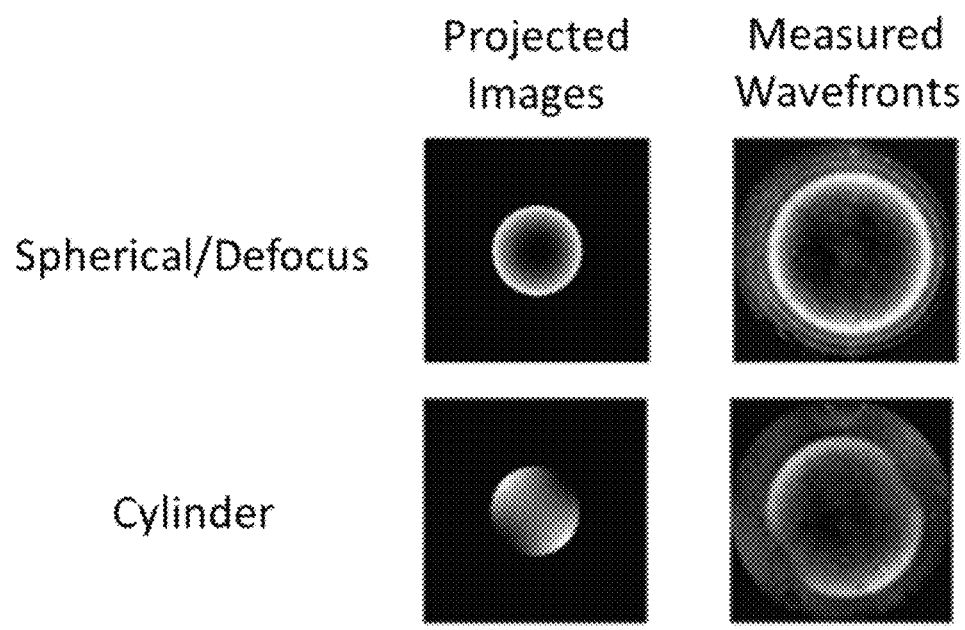
FIG. 9 – Spherical/Defocus and Cylindrical Projected Images and Measured Wavefronts

AMIDE-FUNCTIONALIZED POLYMERIZATION INITIATORS AND THEIR USE IN THE MANUFACTURE OF OPHTHALMIC LENSES

RELATED APPLICATIONS

This application claims priority to U.S. Provisional Patent Application Ser. No. 63/249,646, filed Sep. 29, 2021, which is incorporated herein by reference in its entirety.

FIELD OF THE INVENTION

The invention relates generally to the field of ophthalmic lenses, and more specifically to compositions and methods for imparting various properties and attributes into ophthalmic lenses formed using cast molding techniques.

BACKGROUND OF THE INVENTION

The use of ophthalmic lenses to correct vision is common in today's world. The traditional and most common method for making soft contact lenses is via cast molding techniques, where a polymerizable liquid is placed between two mold halves that together form the shape of the desired lens, and the entirety of the liquid is cured between the mold halves. The lens is then removed from the mold, and certain post processing steps are taken.

More recently, a new system and method for manufacturing contact lenses has been disclosed in which an infinite number of truly custom lenses can readily be produced in a cost-effective manner. U.S. Pat. No. 8,317,505, which is incorporated herein by reference in its entirety, discloses a method for growing a "Lens Precursor Form" on a single male mold or optical mandrel on a Voxel by Voxel basis by selectively projecting actinic radiation through the optic mandrel and into a vat or bath of a photocurable reactive monomer mixture. The optical mandrel and Lens Precursor Form are then removed from the vat and inverted so that the convex surface of the optic mandrel is upright. Following a dwell period during which uncured residual liquid from the bath that remains on the Lens Precursor Form flows under gravity or otherwise over the Lens Precursor Form, the remaining liquid is then cured by applying a fixing radiation to form the final lens. As described therein, the system utilizes a single mold rather than two mold halves as in traditional cast molding, and allows a truly custom lens to be produced by simply "re-programming" the software instructions rather than changing equipment or parts.

As described in the '505 patent, the actinic radiation is projected through the male mold and into the reactive mixture at an array of distinct locations, each of which is selectively controllable, to selectively cure the reactive mixture to a pre-determined depth at any point within the array (on a "voxel by voxel basis"), thereby "growing" the lens from the convex side of the male mold. The term "Voxel" as used herein is the same as in the '505 patent, and refers to a volume element, representing a value on a regular grid in three-dimensional space. A Voxel can be viewed as a three-dimensional pixel, with each Voxel being associated with a particular point in the selectively controllable array.

While the '505 represents a significant advance in lens manufacturing capabilities, further developments are still needed to, for instance, expand the options for making customizable lenses that incorporate functional features to further enhance a lens wearer's experience.

SUMMARY OF THE INVENTION

The invention as described in this disclosure includes novel compositions that may be used as polymerization initiators in the methods described herein and described in Applicants' concurrently filed U.S. patent application, titled "OPHTHALMIC LENSES AND THEIR MANUFACTURE BY IN-MOLD MODIFICATION" naming Michael Widman; Ghulam Maharvi; Shivkumar Mahadevan; Azaam Alli; Alex Guzman; Xin Wei; and Minghan Chen as inventors, which is incorporated herein by reference in its entirety. Such methods leverage the technology described in detail in the '505 patent to provide new compositions and methods for spatially incorporating functional moieties, geometries and/or physical properties into an ophthalmic lens that is made via cast molding.

The invention has particular application for spatially controlling and imparting a variety of properties into a lens made via cast molding without costly process modifications. The compounds of the invention contain a refractive index modifying segment (the amide-containing segment) and a polymerization initiator segment. Thus the invention enables, for instance, use of the compounds for spatial incorporation into a lens to impart refractive index properties. Such properties may provide personalized patient solutions for conditions such as presbyopia.

Thus, in one aspect, the invention provides compounds that may be used as polymerization initiators in the ophthalmic lens manufacturing methods described herein and in Applicant's concurrently filed U.S. patent application. The compounds of the invention are of formula I.

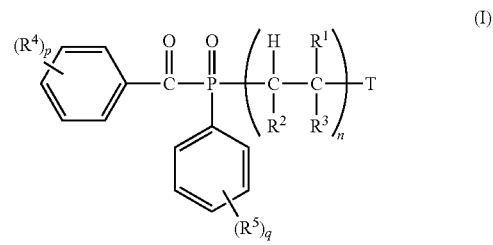

(I)

wherein $R^1$, $R^2$, $R^3$, $R^4$, $R^5$, T, p, q, and n are as defined herein.

In another aspect, the invention provides a method for forming an ophthalmic lens. The method comprises: (a) providing a mold assembly comprised of a base curve and a front curve, the base curve and the front curve defining and enclosing a cavity therebetween, the cavity containing a reactive monomer mixture, wherein the reactive monomer mixture comprises a monomer suitable for making the ophthalmic lens, a first polymerization initiator that is capable of being activated at a first wavelength, a first functional moiety chemically linked to the first polymerization initiator, and a second polymerization initiator that is capable of being activated by a second activation that does not substantially activate the first polymerization initiator, wherein at least one of the base curve or front curve is light transmissive; (b) exposing one or more selective regions of the reactive monomer mixture to a source of actinic radiation at the first wavelength to thereby selectively polymerize a portion of the reactive monomer mixture, wherein the selectively polymerized portion incorporates the first functional moiety; (c) exposing the reactive monomer mixture to the second activation to activate the second polymerization initiator and cure the reactive monomer mixture; (d) removing the ophthalmic lens from the mold assembly; and (e) extracting unreacted first polymerization initiator from the ophthalmic lens, wherein the first polymerization initiator having a chemically linked first functional moiety is a compound of formula I as described herein.

In a further aspect, the invention provides a reactive monomer mixture for making an ophthalmic lens. The reactive monomer mixture comprises: a monomer suitable for making the ophthalmic lens; a first polymerization initiator capable of being activated at a first wavelength; a first functional moiety chemically linked to the first polymerization initiator; and a second polymerization initiator that is capable of being activated by a second activation that does not substantially activate the first polymerization initiator, wherein the first polymerization initiator having a chemically linked first functional moiety is a compound of formula I as described herein.

BRIEF DESCRIPTION OF DRAWINGS

FIG. 4 shows the 500 MHz $^1$H-NMR spectrum of MAPO-PVP in deuterium oxide.

FIG. 5 shows SEC-MALS chromatograms of MAPO-PVP, PVP K30, and PVP K12.

FIG. 6 shows the 500 MHz $^1$H-NMR spectrum of MAPO-PDMA in deuterated methanol.

FIG. 7 shows the USAF 1951 test chart.

FIG. 8 shows the imparted USAF 1951 test chart image on a contact lens.

FIG. 9 shows the spherical/defocus and cylindrical projected images and measure wavefronts.

DETAILED DESCRIPTION OF THE INVENTION

Figure 1:
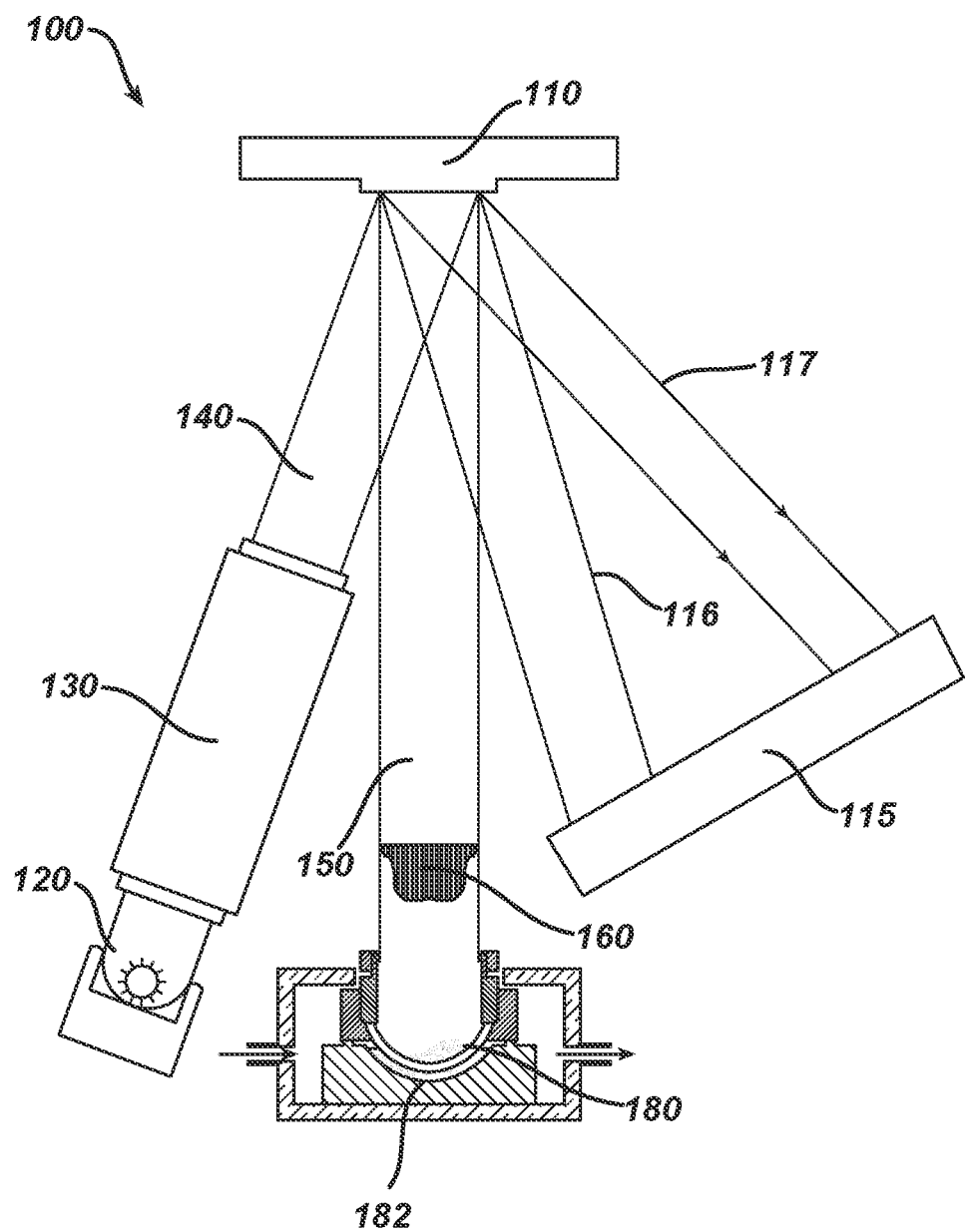
FIG. 1 illustrates a prior art apparatus for forming a custom contact lens.

Unless defined otherwise, all technical and scientific terms used herein have the same meaning as commonly understood by one of ordinary skill in the art to which the invention belongs. All publications, patent applications, patents, and other references mentioned herein are incorporated by reference.

Unless otherwise indicated, numeric ranges, for instance as in "from 2 to 10" or as in "between 2 and 10" are inclusive of the numbers defining the range (e.g., 2 and 10).

Unless otherwise indicated, ratios, percentages, parts, and the like are by weight.

The phrase "number average molecular weight" refers to the number average molecular weight ($M_n$) of a sample; the phrase "weight average molecular weight" refers to the weight average molecular weight ($M_w$) of a sample; the phrase "polydispersity index" (PDI) refers to the ratio of $M_w$ divided by $M_n$ and describes the molecular weight distribution of a sample. If the type of "molecular weight" is not indicated or is not apparent from the context, then it is intended to refer to number average molecular weight.

As used herein, the term "about" refers to a range of +/−10 percent of the number that is being modified. For example, the phrase "about 10" would include both 9 and 11.

As used herein, the term "(meth)" designates optional methyl substitution. Thus, a term such as "(meth)acrylate" denotes both methacrylate and acrylate.

Wherever chemical structures are given, it should be appreciated that alternatives disclosed for the substituents on the structure may be combined in any combination. Thus, if a structure contained substituents R* and R**, each of which contained three lists of potential groups, 9 combinations are disclosed. The same applies for combinations of properties.

The average number of repeating units in a polymer sample is known as its "degree of polymerization." When a generic chemical formula of a polymer sample, such as [***]n is used, "n" refers to its degree of polymerization, and the formula shall be interpreted to represent the number average molecular weight of the polymer sample.

As used herein, the term "individual" includes humans and vertebrates.

As used herein, the term "ophthalmic device" refers to any device which resides in or on the eye or any part of the eye, including the ocular surface. These devices can provide optical correction, cosmetic enhancement, vision enhancement, therapeutic benefit (for example as bandages) or delivery of active components such as pharmaceutical and nutraceutical components, or a combination of any of the foregoing. Preferred ophthalmic devices are ophthalmic lenses, which include soft contact lenses, hard contact lenses (including rigid gas permeable lenses), hybrid contact lenses, intraocular lenses, and inlay and overlay lenses. The ophthalmic device preferably may comprise a contact lens.

As used herein, the term "contact lens" refers to an ophthalmic device that can be placed on the cornea of an individual's eye. The contact lens may correct for refractive errors thereby improving vision, may absorb ultraviolet or visible light thereby providing protection or color enhancement, and may also provide cosmetic benefits such as changing the color and pattern of a wearer's iris. A contact lens can be of any appropriate material known in the art and can be a soft lens, a hard lens, or a hybrid lens containing at least two distinct portions with different physical, mechanical, or optical properties, such as modulus, water content, light transmission, or combinations thereof.

The ophthalmic devices, ophthalmic lenses, and contact lenses of the invention may be comprised of silicone hydrogels. These silicone hydrogels typically contain at least one hydrophilic component and at least one silicone-containing component that are covalently bound to one another in the cured device. The ophthalmic devices, ophthalmic lenses and contact lenses of the invention may also be comprised of conventional hydrogels, or combination of conventional and silicone hydrogels.

A "macromolecule" is an organic compound having a number average molecular weight of greater than 1500 and may be reactive or non-reactive.

As used herein, the "target macromolecule" is the intended macromolecule being synthesized from the reactive composition comprising monomers, macromers, prepolymers, cross-linkers, initiators, additives, diluents, and the like.

As used herein, a "monomer" is a mono-functional molecule which can undergo chain growth polymerization, and in particular, free radical polymerization, thereby creating a repeating unit in the chemical structure of the target macromolecule. Some monomers have di-functional impurities that can act as cross-linking agents. A "hydrophilic monomer" is also a monomer which yields a clear single phase solution when mixed with deionized water at 25° C. at a concentration of 5 weight percent. A "hydrophilic component" is a monomer, macromer, prepolymer, initiator, crosslinker, additive, or polymer which yields a clear single phase solution when mixed with deionized water at 25° C. at a concentration of 5 weight percent. A hydrophilic component may contain at least one polymerizable group. A hydrophilic component may preferably consist of one polymerizable group.

As used herein, a "macromonomer" or "macromer" is a linear or branched macromolecule having at least one polymerizable group that can undergo chain growth polymerization, and in particular, free radical polymerization.

As used herein, the term "polymerizable" means that the compound comprises at least one polymerizable group. "Polymerizable groups" are groups that can undergo chain growth polymerization, such as free radical and/or cationic polymerization, for example a carbon-carbon double bond group which can polymerize when subjected to radical polymerization initiation conditions. Non-limiting examples of polymerizable groups include (meth)acrylates, styrenes, vinyl ethers, (meth)acrylamides, N-vinyllactams, N-vinylamides, 0-vinylcarbamates, 0-vinylcarbonates, and other vinyl groups. Preferably, the polymerizable groups comprise (meth)acrylates, (meth)acrylamides, and mixtures thereof. Preferably, the polymerizable groups comprise (meth)acrylate, (meth)acrylamide, N-vinyl lactam, N-vinylamide, styryl functional groups, or mixtures of any of the foregoing. The polymerizable group may be unsubstituted or substituted. For instance, the nitrogen atom in (meth)acrylamide may be bonded to a hydrogen, or the hydrogen may be replaced with alkyl or cycloalkyl (which themselves may be further substituted). In contrast to "polymerizable," the term "non-polymerizable" means that the compound does not comprise such a free radical polymerizable group.

Examples of the foregoing include substituted or unsubstituted $C_{1-6}$alkyl(meth)acrylates, $C_{1-6}$alkyl(meth)acrylamides, $C_{2-12}$alkenyls, $C_{2-12}$alkenylphenyls, $C_{2-12}$alkenylnaphthyls, $C_{2-6}$alkenylphenyl$C_{1-6}$alkyls, where suitable substituents on said $C_{1-6}$ alkyls include ethers, hydroxyls, carboxyls, halogens and combinations thereof.

Any type of free radical polymerization may be used including but not limited to bulk, solution, suspension, and emulsion as well as any of the controlled radical polymerization methods such as stable free radical polymerization, nitroxide-mediated living polymerization, atom transfer radical polymerization, reversible addition fragmentation chain transfer polymerization, organotellurium mediated living radical polymerization, and the like.

In free radical polymerization, in the absence of chain transfer reactions, propagating chains may terminate by radical coupling or disproportionation. In coupling, two propagating chains simply combine to form a single bond, and the resulting polymer has end-groups composed of initiator fragments. In disproportionation, one propagating chain radical extracts a proton from another propagating chain, adjacent to its free radical, which in turn forms a terminal double bond. Chain transfer reactions may occur with any component in the reaction mixture, such as chain transfer to monomer, chain transfer to polymer which leads to branching, chain transfer to initiator, etc., as well as chain transfer to any intentionally added chain transfer agent to reduce and control the molecular weight. In most chain transfer reactions, the propagating chain extracts a proton from another molecule, thereby terminating chain growth and simultaneously creating another radical. The term "chain terminating group" refers to the chemical group that ends chain growth and becomes one end-group of the final polymer. In most cases, the chain terminating group is a proton, but others are known or thought to occur, such as chain transfer to a peroxide initiator in which the chain terminating group depends on the peroxide, for instance, in the case of benzoyl peroxide, the chain terminating group is benzoate.

As used herein, a "silicone-containing component" or "silicone component" is a monomer, macromer, prepolymer, cross-linker, initiator, additive, or polymer in the reactive composition with at least one silicon-oxygen bond, typically in the form of siloxy groups, siloxane groups, carbosiloxane groups, and mixtures thereof. Examples of silicone-containing components which are useful in this invention may be found in U.S. Pat. Nos. 3,808,178, 4,120,570, 4,136,250, 4,153,641, 4,740,533, 5,034,461, 5,070,215, 5,244,981, 5,314,960, 5,331,067, 5,371,147, 5,760,100, 5,849,811, 5,962,548, 5,965,631, 5,998,498, 6,367,929, 6,822,016, 6,943,203, 6,951,894, 7,052,131, 7,247,692, 7,396,890, 7,461,937, 7,468,398, 7,538,146, 7,553,880, 7,572,841, 7,666,921, 7,691,916, 7,786,185, 7,825,170, 7,915,323, 7,994,356, 8,022,158, 8,163,206, 8,273,802, 8,399,538, 8,415,404, 8,420,711, 8,450,387, 8,487,058, 8,568,626, 8,937,110, 8,937,111, 8,940,812, 8,980,972, 9,056,878, 9,125,808, 9,140,825, 9,156,934, 9,170,349, 9,217,813, 9,244,196, 9,244,197, 9,260,544, 9,297,928, 9,297,929, and European Patent No. 080539. These patents are hereby incorporated by reference in their entireties. A silicone-containing component may contain at least one polymerizable group. A silicone-containing component may preferably consist of one or two polymerizable groups.

A "polymer" is a target macromolecule composed of the repeating units of the monomers and macromers used during polymerization.

A "homopolymer" is a polymer made from one monomer; a "copolymer" is a polymer made from two or more monomers; a "terpolymer" is a polymer made from three monomers. A "block copolymer" is composed of compositionally different blocks or segments. Diblock copolymers have two blocks. Triblock copolymers have three blocks. "Comb or graft copolymers" are made from at least one macromer.

A "repeating unit" is the smallest group of atoms in a polymer that corresponds to the polymerization of a specific monomer or macromer.

An "initiator" is a molecule that can decompose into free radical groups which can react with a monomer to initiate a free radical polymerization reaction. A thermal initiator decomposes at a certain rate depending on the temperature; typical examples are azo compounds such as azobisisobutyronitrile and 4,4'-aobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A photo-initiator decomposes by a photochemical process; typical examples are derivatives of benzil, benzoin, acetophenone, benzophenone, camphorquinone, and mixtures thereof as well as various monoacyl and bisacyl phosphine oxides and combinations thereof.

A "free radical group" is a molecule that has an unpaired valence electron which can react with a polymerizable group to initiate a free radical polymerization reaction.

A "cross-linking agent" or "crosslinker" is a di-functional or multi-functional monomer which can undergo free radical polymerization at two or more locations on the molecule, thereby creating branch points and a polymeric network. The two or more polymerizable functionalities on the crosslinker may be the same or different and may, for instance, be independently selected from vinyl groups (including allyl), (meth)acrylate groups, and (meth)acrylamide groups. Common examples are ethylene glycol dimethacrylate, tetraethylene glycol dimethacrylate, trimethylolpropane trimethacrylate, methylene bisacrylamide, triallyl cyanurate, and the like.

A "prepolymer" is a reaction product of monomers (or macromers) which contains remaining polymerizable groups capable of undergoing further reaction to form a polymer.

A "polymeric network" is a type of polymer that is in the form of a cross-linked macromolecule. Generally, a polymeric network may swell but cannot dissolve in solvents. For instance, the crosslinked substrate network of the invention is a material that is swellable, without dissolving.

"Hydrogels" are polymeric networks that swell in water or aqueous solutions, typically absorbing at least 10 weight percent water (at 25° C.). "Silicone hydrogels" are hydrogels that are made from at least one silicone-containing component with at least one hydrophilic component. Hydrophilic components may also include non-reactive polymers.

"Conventional hydrogels" refer to polymeric networks made from monomers without any siloxy, siloxane or carbosiloxane groups. Conventional hydrogels are prepared from reactive compositions predominantly containing hydrophilic monomers, such as 2-hydroxyethyl methacrylate ("HEMA"), N-vinyl pyrrolidone ("NVP"), N, N-dimethylacrylamide ("DMA") or vinyl acetate.

As used herein, the term "reactive composition" refers to a composition containing one or more reactive components (and optionally non-reactive components) which are mixed (when more than one is present) together and, when subjected to polymerization conditions, form polymer compositions. If more than one component is present, the reactive composition may also be referred to herein as a "reactive mixture" or a "reactive monomer mixture" (or RMM). The reactive composition comprises reactive components such as the monomers, macromers, prepolymers, cross-linkers, and initiators, and optional additives such as wetting agents, release agents, dyes, light absorbing compounds such as UV-VIS absorbers, pigments, dyes and photochromic compounds, any of which may be reactive or non-reactive but are preferably capable of being retained within the resulting polymer composition, as well as pharmaceutical and nutraceutical compounds, and any diluents. It will be appreciated that a wide range of additives may be added based upon the final product which is made and its intended use. Concentrations of components of the reactive composition are expressed as weight percentages of all components in the reaction composition, excluding diluent. When diluents are used, their concentrations are expressed as weight percentages based upon the amount of all components in the reaction composition and the diluent.

"Reactive components" are the components in the reactive composition which become part of the chemical structure of the resulting material by covalent bonding, hydrogen bonding, electrostatic interactions, the formation of interpenetrating polymeric networks, or any other means. Examples include but are not limited to silicone reactive components (e.g., the silicone-containing components described below) and hydrophilic reactive components (e.g., the hydrophilic monomers described below).

As used herein, the term "silicone hydrogel contact lens" refers to a contact lens comprising at least one silicone hydrogel. Silicone hydrogel contact lenses generally have increased oxygen permeability compared to conventional hydrogels. Silicone hydrogel contact lenses use both their water and polymer content to transmit oxygen to the eye.

"DMD" refers to a digital micromirror device that may be a bistable spatial light modulator consisting of an array of movable micromirrors functionally mounted over a CMOS SRAM. Each mirror may be independently controlled by loading data into the memory cell, which may be below the mirror, to steer reflected light, spatially mapping a pixel of video data to a pixel on a display. The data electrostatically controls the mirror's tilt angle in a binary fashion, where the mirror states are either +X degrees (on) or −X degrees (off). Light reflected by the on mirrors then may be passed through a projection lens and onto a screen. Light may be reflected off to create a dark field and defines the black-level floor for the image. Images may be created by gray-scale modulation between on and off levels at a rate fast enough to be integrated by the observer. The DMD (digital micromirror device) may comprise Digital Light Processing (DLP) projection systems.

"DMD Script" refers to a control protocol and image file for a spatial light modulator and also to the control signals of any system component, for example, a light source or filter wheel, either of which may include a series of command sequences in time.

The term "multi-functional" refers to a component having two or more polymerizable groups. The term "mono-functional" refers to a component having one polymerizable group.

The terms "halogen" or "halo" indicate fluorine, chlorine, bromine, and iodine.

As used herein, the term "alkyl" refers to an unsubstituted or substituted linear or branched alkyl group containing the indicated number of carbon atoms. If no number is indicated, then alkyl (optionally including any substituents on alkyl) may contain 1 to 16 carbon atoms. Preferably, the alkyl group contains 1 to 10 carbon atoms, alternatively 1 to 7 carbon atoms, or alternatively 1 to 4 carbon atoms. Examples of alkyl include methyl, ethyl, propyl, isopropyl, butyl, iso-, sec- and tert-butyl, pentyl, hexyl, heptyl, 3-ethylbutyl, and the like. Examples of substituents on alkyl include 1, 2, or 3 groups independently selected from hydroxy, amino, amido, oxa, carboxy, alkyl carboxy, carbonyl, alkoxy, amido, carbamate, carbonate, halogen, phenyl, benzyl, and combinations thereof "Alkylene" means a divalent alkyl group, such as —$CH_2$—, —$CH_2CH_2$—, —$CH_2CH_2CH_2$—, —$CH_2CH(CH_3)CH_2$—, and —$CH_2CH_2CH_2CH_2$—.

"Haloalkyl" refers to an alkyl group as defined above substituted with one or more halogen atoms, where each halogen is independently F, Cl, Br or I. A preferred halogen is F. Preferred haloalkyl groups contain 1-6 carbons, more preferably 1-4 carbons, and still more preferably 1-2 carbons. "Haloalkyl" includes perhaloalkyl groups, such as —$CF_3$— or —$CF_2CF_3$—. "Haloalkylene" means a divalent haloalkyl group, such as —$CH_2CF_2$—.

"Cycloalkyl" refers to an unsubstituted or substituted cyclic hydrocarbon containing the indicated number of ring carbon atoms. If no number is indicated, then cycloalkyl may contain 3 to 12 ring carbon atoms. Preferred are $C_3$-$C_8$ cycloalkyl groups, more preferably $C_4$-$C_7$ cycloalkyl, and still more preferably $C_5$-$C_6$ cycloalkyl. Examples of cycloalkyl include cyclopropyl, cyclobutyl, cyclopentyl, cyclohexyl, cycloheptyl and cyclooctyl. Examples of substituents on cycloalkyl include 1, 2, or 3 groups independently selected from alkyl, hydroxy, amino, amido, oxa, carbonyl, alkoxy, amido, carbamate, carbonate, halo, phenyl, benzyl, and combinations thereof. "Cycloalkylene" means a divalent cycloalkyl group, such as 1,2-cyclohexylene, 1,3-cyclohexylene, or 1,4-cyclohexylene.

"Heterocycloalkyl" refers to a cycloalkyl ring or ring system as defined above in which at least one ring carbon has been replaced with a heteroatom selected from nitrogen, oxygen, and sulfur. The heterocycloalkyl ring is optionally fused to or otherwise attached to other heterocycloalkyl rings and/or non-aromatic hydrocarbon rings and/or phenyl rings. Preferred heterocycloalkyl groups have from 5 to 7 members. More preferred heterocycloalkyl groups have 5 or 6 members. Heterocycloalkylene means a divalent heterocycloalkyl group.

"Aryl" refers to an unsubstituted or substituted aromatic hydrocarbon ring system containing at least one aromatic ring. The aryl group contains the indicated number of ring carbon atoms. If no number is indicated, then aryl may contain 6 to 14 ring carbon atoms. The aromatic ring may optionally be fused or otherwise attached to other aromatic hydrocarbon rings or non-aromatic hydrocarbon rings. Examples of aryl groups include phenyl, naphthyl, and biphenyl. Preferred examples of aryl groups include phenyl. Examples of substituents on aryl include 1, 2, or 3 groups independently selected from alkyl, hydroxy, amino, amido, oxa, carboxy, alkyl carboxy, carbonyl, alkoxy, amido, carbamate, carbonate, halo, phenyl, benzyl, and combinations thereof. "Arylene" means a divalent aryl group, for example 1,2-phenylene, 1,3-phenylene, or 1,4-phenylene.

"Heteroaryl" refers to an aryl ring or ring system, as defined above, in which at least one ring carbon atom has been replaced with a heteroatom selected from nitrogen, oxygen, and sulfur. The heteroaryl ring may be fused or otherwise attached to one or more heteroaryl rings, aromatic or nonaromatic hydrocarbon rings or heterocycloalkyl rings. Examples of heteroaryl groups include pyridyl, furyl, and thienyl. "Heteroarylene" means a divalent heteroaryl group.

"Alkoxy" refers to an alkyl group attached to the parent molecular moiety through an oxygen bridge. Examples of alkoxy groups include, for instance, methoxy, ethoxy, propoxy and isopropoxy. "Aryloxy" refers to an aryl group attached to a parent molecular moiety through an oxygen bridge. Examples include phenoxy. "Cyclic alkoxy" means a cycloalkyl group attached to the parent moiety through an oxygen bridge.

"Alkylamine" refers to an alkyl group attached to the parent molecular moiety through an —NH— bridge. Alkyleneamine means a divalent alkylamine group, such as —$CH_2CH_2NH$—.

"Siloxanyl" refers to a structure having at least one Si—O—Si bond. Thus, for example, siloxanyl group means a group having at least one Si—O—Si group (i.e. a siloxane group), and siloxanyl compound means a compound having at least one Si—O—Si group. "Siloxanyl" encompasses monomeric (e.g., Si—O—Si) as well as oligomeric/polymeric structures (e.g., —[Si—O]$_n$—, where n is 2 or more). Each silicon atom in the siloxanyl group is substituted with independently selected $R^A$ groups (where $R^A$ is as defined in formula A options (b)-(i)) to complete their valence.

"Silyl" refers to a structure of formula $R_3Si$— and "siloxy" refers to a structure of formula $R_3Si$—O—, where each R in silyl or siloxy is independently selected from trimethylsiloxy, $C_1$-$C_8$ alkyl (preferably $C_1$-$C_3$ alkyl, more preferably ethyl or methyl), and $C_3$-$C_8$ cycloalkyl.

"Alkyleneoxy" refers to groups of the general formula -(alkylene-O)$_p$— or —(O-alkylene)$_p$-, wherein alkylene is as defined above, and p is from 1 to 200, or from 1 to 100, or from 1 to 50, or from 1 to 25, or from 1 to 20, or from 1 to 10, wherein each alkylene is independently optionally substituted with one or more groups independently selected from hydroxyl, halo (e.g., fluoro), amino, amido, ether, carbonyl, carboxyl, and combinations thereof. If p is greater than 1, then each alkylene may be the same or different and the alkyleneoxy may be in block or random configuration. When alkyleneoxy forms a terminal group in a molecule, the terminal end of the alkyleneoxy may, for instance, be a hydroxy or alkoxy (e.g., HO—[$CH_2CH_2O$]$_p$— or $CH_3O$—[$CH_2CH_2O$]$_p$—). Examples of alkyleneoxy include polymethyleneoxy, polyethyleneoxy, polypropyleneoxy, polybutyleneoxy, and poly(ethyleneoxy-co-propyleneoxy).

"Oxaalkylene" refers to an alkylene group as defined above where one or more non-adjacent $CH_2$ groups have been substituted with an oxygen atom, such as —$CH_2CH_2OCH(CH_3)CH_2$—. "Thiaalkylene" refers to an alkylene group as defined above where one or more non-adjacent $CH_2$ groups have been substituted with a sulfur atom, such as —$CH_2CH_2SCH(CH_3)CH_2$—.

The term "linking group" refers to a moiety that links the polymerizable group to the parent molecule. The linking group may be any moiety that does not undesirably interfere with the polymerization of the compound of which it is a part. For instance, the linking group may be a bond, or it may comprise one or more alkylene, haloalkylene, amide, amine, alkyleneamine, carbamate, carboxylate (—$CO_2$—), arylene, heteroarylene, cycloalkylene, heterocycloalkylene, alkyleneoxy, oxaalkylene, thiaalkylene, haloalkyleneoxy (alkyleneoxy substituted with one or more halo groups, e.g., —$OCF_2$—, —$OCF_2CF_2$—, —$OCF_2CH_2$—), siloxanyl, alkylenesiloxanyl, or combinations thereof. The linking group may optionally be substituted with 1 or more substituent groups. Suitable substituent groups may include those independently selected from alkyl, halo (e.g., fluoro), hydroxyl, HO-alkyleneoxy, MeO-alkyleneoxy, siloxanyl, siloxy, siloxy-alkyleneoxy-, siloxy-alkylene-alkyleneoxy- (where more than one alkyleneoxy groups may be present and wherein each methylene in alkylene and alkyleneoxy is independently optionally substituted with hydroxyl), ether, amine, carbonyl, carbamate, and combinations thereof. The linking group may also be substituted with a polymerizable group, such as (meth)acrylate.

Preferred linking groups include $C_1$-$C_8$ alkylene (preferably $C_2$-$C_6$ alkylene) and $C_1$-$C_8$ oxaalkylene (preferably $C_2$-$C_6$ oxaalkylene), each of which is optionally substituted with 1 or 2 groups independently selected from hydroxyl and siloxy. Preferred linking groups also include carboxylate, amide, $C_1$-$C_8$ alkylene-carboxylate-$C_1$-$C_8$ alkylene, or $C_1$-$C_8$ alkylene-amide-$C_1$-$C_8$ alkylene.

When the linking group is comprised of combinations of moieties as described above (e.g., alkylene and cycloalkylene), the moieties may be present in any order. For instance, if in Formula E below, L (linking group) in a structural formula is indicated as being -alkylene-cycloalkylene-, then Rg-L may be either Rg-alkylene-cycloalkylene-, or Rg-cycloalkylene-alkylene-. Notwithstanding this, the listing order represents the preferred order in which the moieties appear in the compound starting from the terminal polymerizable group (Rg) to which the linking group is attached. For example, if two linking groups, L and $L^2$, are indicated as both being alkylene-cycloalkylene, then Rg-L is preferably Rg-alkylene-cycloalkylene- and -$L^2$-Rg is preferably -cycloalkylene-alkylene-Rg.

As noted above, in one aspect, the invention provides compounds that are useful for the manufacture of ophthalmic lenses. The compounds are of the formula I:

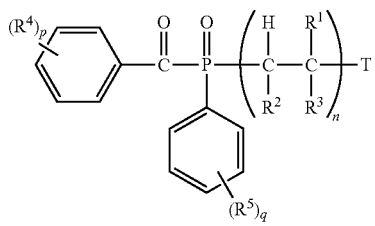

(I)

wherein $R^1$ at each occurrence is independently H or methyl; $R^2$ and $R^3$ at each occurrence are independently H or —X'—N($R^6$)($R^7$), provided that at least one $R^2$ or $R^3$ is —X'—N($R^6$)($R^7$), wherein X' at each occurrence is independently a bond or —(CO)—, $R^6$ at each occurrence is independently H, $C_1$-$C_6$ alkyl, or $C_1$-$C_6$ alkylcarbonyl and $R^7$ at each occurrence is independently H, $C_1$-$C_6$ alkyl, or $C_1$-$C_6$ alkylcarbonyl, or $R^6$ and $R^7$ at any occurrence, together with the nitrogen atom to which they are bonded, form a heterocycloalkyl ring in which a ring carbon atom is optionally replaced with a heteroatom selected from nitrogen, oxygen, and sulfur, wherein each alkyl and alkylcarbonyl is independently optionally substituted with hydroxy, amino, amido, oxo, carboxy, alkyl carboxy, carbonyl, alkylcarbonyl, alkoxy, amido, carbamate, carbonate, halo, phenyl, or benzyl, and each heterocycloalkyl is independently optionally substituted with alkyl, hydroxy, amino, amido, oxo, carboxy, alkyl carboxy, carbonyl, alkylcarbonyl, alkoxy, amido, carbamate, carbonate, halo, phenyl, or benzyl; $R^4$ and $R^5$, when present, are independently at each occurrence alkyl, cycloalkyl, alkoxy, or halo; T is a chain termination group; n is from 10 to 4000; and p and q are independently 0, 1, 2, 3, 4, or 5.

Compounds of formula I may include compounds of formula I-1, which are compounds of formula I wherein one of $R^2$ and $R^3$ at each occurrence is H.

Compounds of formulae I and I-1 may include compounds of formula I-2, which are compounds of formula I or I-1 wherein q is 0.

Compounds of formulae I, I-1, and I-2 may include compounds of formula I-3, which are compounds of formula I, I-1, or I-2 wherein p is 3 and $R^4$ at each occurrence is independently $C_1$-$C_3$ alkyl.

Compounds of formulae I, I-1, I-2, and I-3 may include compounds of formula I-4, which are compounds of formula I, I-1, I-2, or I-3 wherein $R^6$ and $R^7$, together with the nitrogen atom to which they are bonded, form a heterocycloalkyl ring optionally substituted with alkyl, hydroxy, amino, amido, oxo, carboxy, alkyl carboxy, carbonyl, alkylcarbonyl, alkoxy, amido, carbamate, carbonate, or halo.

Compounds of formulae I, I-1, I-2, I-3, and I-4 may include compounds of formula I-5, which are compounds of formula I, I-1, I-2, I-3, or I-4 wherein $R^6$ and $R^7$, together with the nitrogen atom to which they are bonded, form imidazolidinyl, piperazinyl, pyrrolidinyl, or piperidinyl optionally substituted with alkyl or oxo.

Compounds of formulae I, I-1, I-2, I-3, I-4, and I-5 may include compounds of formula I-6, which are compounds of formula I, I-1, I-2, I-3, I-4, or I-5 wherein $R^6$ and $R^7$, together with the nitrogen atom to which they are bonded, form 2-pyrrolidinone.

Compounds of formulae I, I-1, I-2, and I-3 may include compounds of formula I-7, which are compounds of formula I, I-1, I-2, or I-3 wherein $R^6$ and $R^7$ are independently H, $C_1$-$C_6$ alkyl, or $C_1$-$C_6$ alkylcarbonyl, wherein alkyl and alkylcarbonyl are independently optionally substituted with hydroxy.

Compounds of formulae I, I-1, I-2, I-3, and I-7 may include compounds of formula I-8, which are compounds of formula I, I-1, I-2, I-3, or I-7 wherein $R^6$ and $R^7$ are independently H or $C_1$-$C_4$ alkyl, wherein alkyl is optionally substituted with hydroxy.

Compounds of formulae I, I-1, I-2, I-3, and I-7 may include compounds of formula I-9, which are compounds of formula I, I-1, I-2, I-3, or I-7 wherein $R^6$ and $R^7$ are both H.

Compounds of formulae I, I-1, I-2, I-3, and I-7 may include compounds of formula I-10, which are compounds of formula I, I-1, I-2, I-3, or I-7 wherein $R^6$ is H and $R^7$ is $C_1$-$C_3$ alkyl or $C_1$-$C_3$ alkylcarbonyl, wherein alkyl is optionally substituted with hydroxy.

Compounds of formulae I, I-1, I-2, I-3, and I-7 may include compounds of formula I-11, which are compounds of formula I, I-1, I-2, I-3, or I-7 wherein $R^6$ and $R^7$ are independently $C_1$-$C_3$ alkyl optionally substituted with hydroxy.

Compounds of formulae I, I-1, I-2, I-3, and I-7 may include compounds of formula I-12, which are compounds of formula I, I-1, I-2, I-3, or I-7 wherein $R^6$ is $C_1$-$C_3$ alkyl optionally substituted with hydroxy and $R^7$ is $C_1$-$C_3$ alkylcarbonyl.

Compounds of formulae I, I-1, I-2, I-3, I-4, I-5, I-6, I-7, I-8, I-9, I-10, I-11, and I-12 may include compounds of formula I-13, which are compounds of formula I, I-1, I-2, I-3, I-4, I-5, I-6, I-7, I-8, I-9, I-10, I-11, or I-12 wherein X' is —(CO)—.

Compounds of formulae I, I-1, I-2, I-3, I-4, I-5, I-6, I-7, I-8, I-9, I-10, I-11, and I-12 may include compounds of formula I-14, which are compounds of formula I, I-1, I-2, I-3, I-4, I-5, I-6, I-7, I-8, I-9, I-10, I-11, or I-12 wherein X' is a direct bond.

Compounds of formulae I, I-1, I-2, I-3, I-4, I-5, I-6, I-7, I-8, I-9, I-10, I-11, I-12, I-13, and I-14 may include compounds of formula I-15, which are compounds of formula I, I-1, I-2, I-3, I-4, I-5, I-6, I-7, I-8, I-9, I-10, I-11, I-12, I-13, or I-14 wherein n ranges from about 100, or from about 200, or from about 300 and up to about 3800, or up to about 3700, or up to about 3500. More preferably, n ranges from about 300 to about 3700.

Example compounds of formula I are shown in Table A.

TABLE A

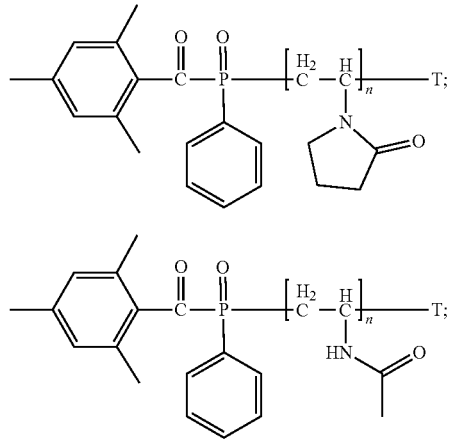

TABLE A-continued

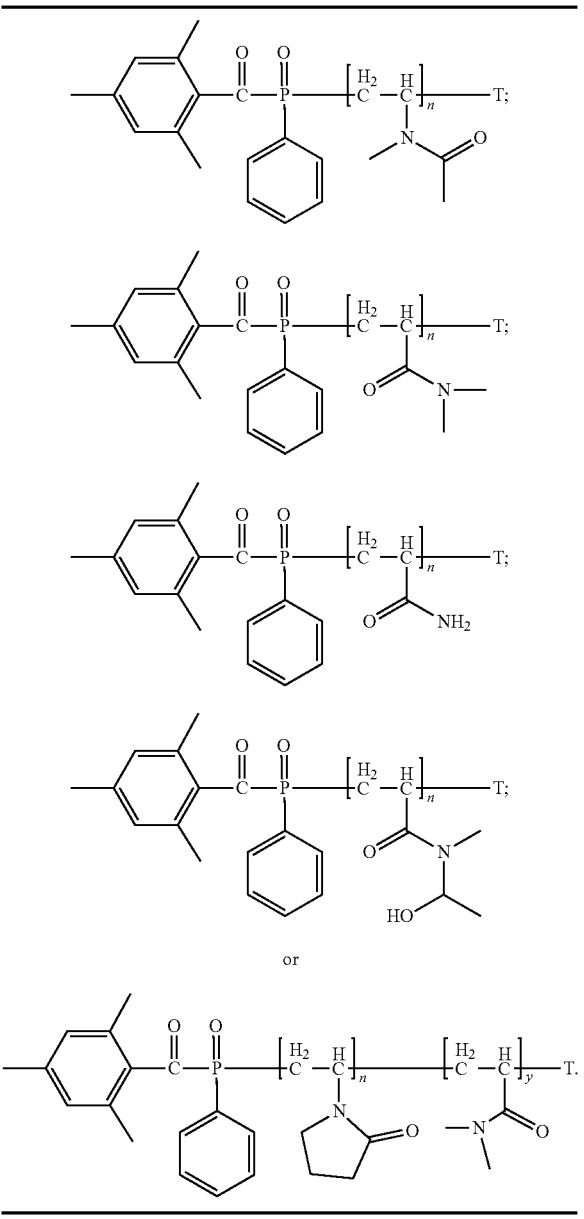

Compounds of formula I may be readily prepared by those skilled in the art using literature methods. Exemplary syntheses are shown in the Examples below.

Compounds of formula I may be used as functionalized photoinitiators for the manufacture of ophthalmic lenses. Such manufacturing method may comprise: (a) providing a mold assembly comprised of a base curve and a front curve, the base curve and the front curve defining and enclosing a cavity therebetween, the cavity containing a reactive monomer mixture, wherein the reactive monomer mixture comprises a monomer suitable for making the ophthalmic lens, a first polymerization initiator that is capable of being activated at a first wavelength, a first functional moiety chemically linked to the first polymerization initiator, and a second polymerization initiator that is capable of being activated by a second activation that does not substantially activate the first polymerization initiator, wherein at least one of the base curve or front curve is light transmissive; (b) exposing one or more selective regions of the reactive monomer mixture to a source of actinic radiation at the first wavelength to thereby selectively polymerize a portion of the reactive monomer mixture, wherein the selectively polymerized portion incorporates the first functional moiety; (c) exposing the reactive monomer mixture to the second activation to activate the second polymerization initiator and cure the reactive monomer mixture; (d) removing the ophthalmic lens from the mold assembly; and (e) extracting unreacted first polymerization initiator (with chemically linked first functional moiety) from the ophthalmic lens, wherein the first polymerization initiator having a chemically linked first functional moiety is a compound of formula I (which may be a compound according to any of the formulas I-1 to I-15 described above or it may be a compound shown in Table A).

According to the method, reactive monomer mixtures are formed into ophthalmic lenses, such as soft contact lenses, by dispensing the mixture into a mold assembly and subsequently curing the mixture. The mold assembly is comprised of a base curve, which is the mold half that contacts the posterior surface of the lens, and a front curve, which contacts the anterior surface. The front curve and base curve, when brought together, define and enclose a cavity between them which, according to the invention, contains the reactive monomer mixture.

The mold components (front curve and base curve), from the which the mold assembly used in the invention is comprised, may be made from various materials, including disposable or reusable materials. For instance, the mold may be a thermoplastic optical mold, made from any suitable material including, without limitation, polyethylene, polypropylene, other polyolefins including homopolymers, copolymers, and terpolymers, polystyrene, polystyrene copolymers, polyesters such as poly(ethylene terephathalate) and poly(butylene terephthalate), polyamides, poly (vinyl alcohol) and its derivatives, hydrogenated styrene butadiene block copolymers like Tuftec, cyclic olefin polymers such as Zeonor and Topas resins, and combinations thereof. The mold may be selected to be transparent or mostly transparent to wavelengths that will activate the first polymerization initiator, thus permitting irradiation through the front curve, the base curve, or both the front curve and base curve. The material may be the same or different between the front and base curves. A preferred material for the front curve of the mold assembly is a 90:10 (w/w) blend of cyclic olefin polymer and hydrogenated styrene butadiene block copolymer, respectively. A preferred material for the base curve of the mold assembly is a 90:10 (w/w) blend of cyclic olefin polymer and polypropylene. Other exemplary materials include a blend of Zeonor and Tuftec for either or both of the base curve and the front curve. The thickness of the base curve or front curve molds may vary, but is typically between 100 and 1500 microns, preferably between 600 and 800 microns, as measured in the center of the optical zone of the target lens mold design. Other mold materials that may be used include re-usable molds comprised of, for instance, glass, quartz, or ceramics such as Aluminum oxide. BK270 and RB 270 are examples of materials suitable for molding for the transmissive mold half They may be molded or polished to achieve acceptable optical profile and surface roughness properties. Additionally, coatings may be applied to such re-usable molds to aid in the release of the cured lens. These mold coatings are typically based on siloxanes or silanes and may be partially or completely fluorinated.

The reactive monomer mixture contains a first polymerization initiator having a first functional moiety chemically linked to it (i.e., a compound of formula I). The first polymerization initiator is capable of being activated at a first wavelength (the wavelength, which may be a range of wavelengths, that activates the first polymerization initiator). As discussed above, when activated by the first wavelength, the polymerization initiator decomposes into free radical groups which can react with a monomer in the reactive monomer mixture to initiate a free radical polymerization reaction. The initiator, once the polymerization is initiated, adds monomer units to grow the polymer chain and, as a result, also becomes a covalently linked part of the polymer. As a consequence, the first functional moiety, which is chemically linked to the initiator, also becomes part of the polymer. The result is the incorporation of the functional moiety into the lens. And because the process of the invention adopts a selective polymerization approach, it is possible to position the functional moiety at specified locations in the ophthalmic lens. Such selective positioning of functional features permits the manufacture of lenses that incorporate modified refractive index features.

The first polymerization initiator (compound of formula I) may absorb (and be activated by) various wavelengths of light, for instant ultraviolet (UV) wavelengths and/or visible light wavelengths. Preferably, the first polymerization initiator may absorb within the visible range (about 380 nm to about 780 nm) of the electromagnetic spectrum. Preferably, the first polymerization initiator is activated at wavelengths including ranges from 200 to 600 nm, or from 300 to 500 nm, or from 350 to 450 nm, or from 380 to 450 nm.

The reactive monomer mixture of contains a first functional moiety that is chemically linked to the first polymerization initiator. As described above, the method permits the incorporation of the first functional moiety at selective locations in the ophthalmic lens. A wide variety of functional moieties may be incorporated. Thus, the first wavelength, and its intensity and pattern, may be selectively chosen to interact with the spectral absorbance of the monomer mixture such that a desired two-dimensional or three-dimensional incorporation of the first functional moiety is achieved via Beer's law effects, as is described in detail in U.S. Pat. No. 8,317,505, which is incorporated herein by reference in its entirety.

The first functional moiety may be designed to affect an overall change in the optical path length with or without a concomitant change in the absorption spectrum in the regions of the hydrated lens that are formed by the first polymerization initiator. In that way, the overall optics of the lens can be modified in a deterministic manner. The optical path length (OPL) is calculated by the formula: $OPL = \int_a^b n(s)ds$ where n(s) is refractive index as a function of distance travelled through a medium (s) where the light path travels between points a and b (see Field Guide to Geometrical Optics, John E. Greivenkamp, Editor, University of Arizona, SPIE Field Guides, Volume FG01, SPIE Press, Bellingham WA, USA, 2004). For homogeneous media, OPL is simply the refractive index times the distance travelled (n times s). In theory, the OPL can be modified by the incorporation of a first functional moiety by either changing the refractive index of the region, by changing the distance travelled by light rays through the region, for instance, by changing the swelling properties of the region based on compositional and/or crosslink density modifications which in turn affect the thickness profile of the optical zone of the lens, or any combination of factors that change the OPL in the region. In this application, the term "refractive index moiety" is defined as a first functional moiety that changes the OPL in part by changing the refractive index of the regions created by activating the first polymerization initiator. The composition of the reactive monomer mixture will determine the impact of swelling and/or crosslink density on the OPL of the regions created by activating the first polymerization initiator.

The compounds of formula I incorporate a first functional moiety which may function as a refractive index moiety. The first functional moiety may be an amide based refractive index moiety. A refractive index moiety alters the OPL of the lens, in the areas where it is incorporated, relative to the bulk lens. Variations in refractive properties across a lens can be used to impart images or other visual features into the lens or to impart features that affect visual function, for example for the purpose of generating bifocal or multifocal lenses.

The compound of formula I may be used as the first polymerization initiator (containing a chemically linked first functional moiety) may be present in the reactive monomer mixture of the method described above in effective amounts of, for instance, 0.01 weight percent to 20 weight percent based on all components in the reactive monomer mixture, excluding diluents.

The reactive monomer mixture of the method contains a second polymerization initiator. The second polymerization initiator is capable of being activated by a second activation that does not substantially activate (e.g., less than 50 mole percent, preferably less than 20 mole percent, more preferably less than 5 mole percent, and further preferably less than 1 mole percent, activation of) the first polymerization initiator. For example, the second polymerization initiator can be activated by either photonic or thermal energy that does not substantially activate the first initiator. Preferably, the second polymerization initiator is a thermal initiator. Examples of thermal initiators include, without limitation, azo compounds such as azobisisobutyronitrile and 4,4'-azobis(4-cyanovaleric acid), peroxides such as benzoyl peroxide, tert-butyl peroxide, tert-butyl hydroperoxide, tert-butyl peroxybenzoate, dicumyl peroxide, and lauroyl peroxide, peracids such as peracetic acid and potassium persulfate as well as various redox systems. A preferred thermal initiator is azobisisobutyronitrile (AIBN). Optionally, the second polymerization initiator may contain a chemically linked second functional moiety, which may be the same or different from the first functional moiety. The second polymerization initiator is used in the reactive monomer mixture in effective amounts to initiate polymerization of the reactive monomer mixture, e.g., from about 0.1 to about 2 parts by weight per 100 parts of reactive monomer mixture.

According to the method, one or more selective regions of the reactive monomer mixture (in the mold assembly cavity) are exposed to a source of actinic radiation at the first wavelength, which thereby selectively activates the first polymerization initiator (the formula I compound) and consequently selectively polymerizes a portion of the reactive monomer mixture. Advantageously, because the first polymerization initiator has the first functional moiety chemically linked to it, the selectively polymerized portion of the reactive monomer mixture incorporates the first functional moiety.

Various techniques may be used for the selective activation of the first polymerization initiator. A preferred technique is voxel-based lithography as generally described, for example, in US20150146159, U.S. Pat. Nos. 9,075,186, and 8,317,505, each of which is incorporated herein by reference in its entirety. Additional references include U.S. Pat. Nos. 7,905,594, 8,157,373, 8,240,849, 8,313,828, 8,318,055, 8,795,558, 9,180,633, 9,180,634, 9,417,464, 9,610,742, and 9,857,607, each of which is incorporated herein by reference in its entirety.

FIG. 1 illustrates an exemplary prior art apparatus described in U.S. Pat. No. 8,317,505 ("the '505 patent") that can be used to selectively control an array of individual beams of actinic radiation to cure or partially cure a reactive monomer mixture such as that used to form ophthalmic lenses. Light is generated by an actinic radiation source or light source 120 and emerges as a light in a defined band of wavelengths but with some spatial variation in intensity and direction. Element 130, a spatial intensity controller or collimator, condenses, diffuses and, in some embodiments, collimates light to create a beam of light 140 that is highly uniform in intensity and preferably centered around a predetermined wavelength. Further, in some embodiments, the beam 140 impinges on a digital micromirror device (DMD) 110 including an array of selectively controllable mirrors, which divides the beam into pixel elements of intensity each of which can be assigned a digital on or off value. In reality, the mirror at each pixel reflects light in one of two paths. The "ON" path (item 150) is the path that leads to photons proceeding toward a reactive chemical media. In the "OFF" path, light is reflected along a different path that will lie between the paths depicted as items 116 and 117. This "OFF" path directs photons to impinge upon a beam dump 115 which has been carefully crafted to absorb and entrap any photons directed towards it. Referring back to the "ON" path 150, light depicted in this path actually includes the many different pixel values that have been set to the "ON" value and are spatially directed along the appropriate individual path corresponding to their pixel location. A time averaged intensity of each of the pixel elements along their respective paths 150 can be represented as a spatial intensity profile 160 across the spatial grid defined by the DMD 110. Alternatively, with the constant intensity impinging on each mirror, item 160 may represent a spatial time exposure profile. The computer program that selectively controls the array of mirrors (on/off time) is referred to herein as a "script".

The '505 patent describes the beams vertically impinging on a light transmissive forming optic 180 and into a volume of reactive monomer mixture 302 (FIG. 2), with the selectively controllable beams of actinic radiation causing selective curing, through the forming optic, of the reactive monomer within the vat on a voxel by voxel basis according to the script.

Figure 2:
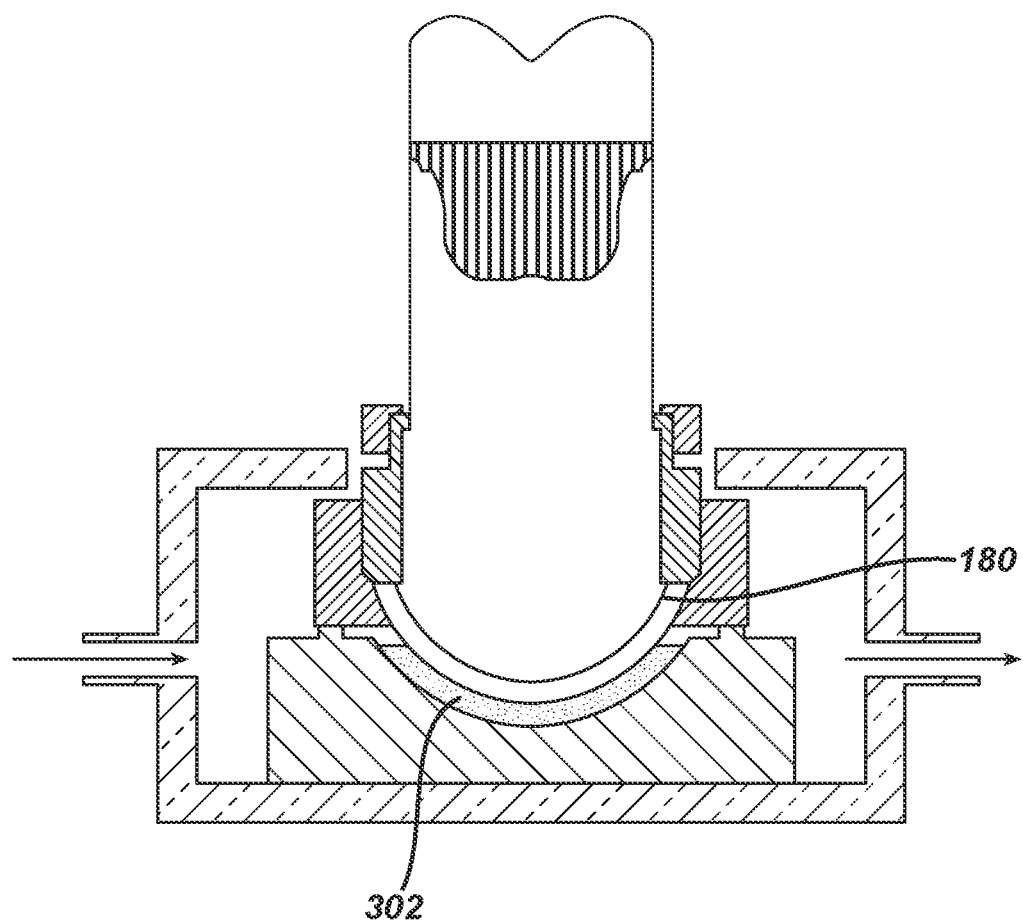
FIG. 2 is an enlarged view of the forming optic portion of the prior art apparatus of FIG. 1.
Figure 3:
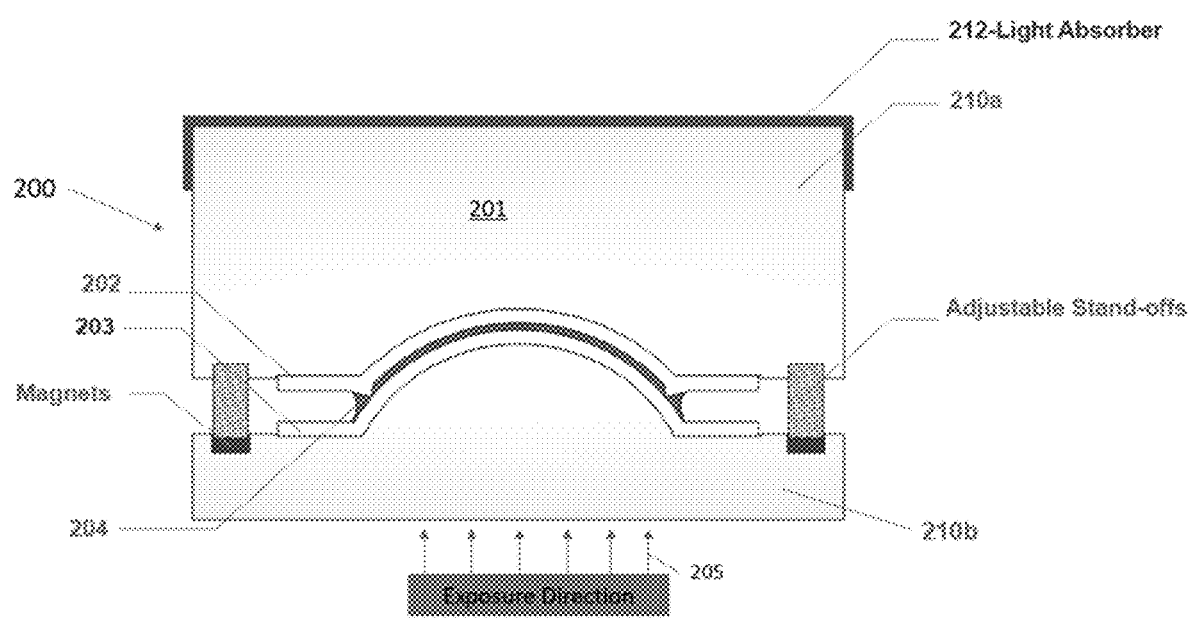
FIG. 3 illustrates an exemplary cure apparatus including a cast mold in an exposure jig that may be used to form a lens in accordance with the system and method described herein.

The method described herein may leverage the apparatus of FIGS. 1 and 2, but replaces the forming optic (male mold) with a traditional two part cast mold such as the exemplary one shown in FIG. 3. As shown in FIG. 3, the cure apparatus 200 including first 201 and second 202 mold halves that together form the shape of the cured contact lens to be formed, at least one of which is light transmissive, with a reactive monomer mixture 204 filling the entire space in between. The first and second mold halves are secured in place within a cure apparatus 200 including a first portion 210a and a second portion 210b, at least one portion of which (i.e., 210b in FIG. 3) is similarly light transmissive. A selectively controllable source of actinic radiation 205, such as that described above, is directed to selectively impinge upon a light transmissive mold half and exposure jig portion as illustrated. The apparatus may further include a light absorber 212 designed to capture stray light after it has passed through the transmissive jig portion, mold half and reactive monomer mixture. In the alternative, the opposing mold half and/or jig portion could be non-transmissive or otherwise light absorbing, such as if the mold half or jig portion was comprised of a carbon black filled thermoplastic such as styrene or polymethyl methacrylate (PMMA).

The method described herein can be used to spatially incorporate (two-dimensional or three-dimensional) functional moieties, geometries, or physical properties into an ophthalmic lens formed between the two mold halves. As discussed above, this can be accomplished by incorporating into the reactive monomer mixture a first polymerization initiator linked to a first functional moiety that is activated by a first predetermined wavelength or range of wavelengths, and a second polymerization initiator linked or not linked to a second functional moiety. The second polymerization initiator can be activated by a second activation that does not substantially activate the first initiator. The second activation may, for instance, be by application of photonic and/or thermal energy. As such the photonic and/or thermal energy can be selectively applied by the cure apparatus to selectively and differentially cure and/or otherwise selectively activate the functional chemistry.

By way of illustration, the reactive monomer mixture can first be exposed to light at a first wavelength or wavelength range via the source of actinic radiation 205 according to a predetermined digital script as described above. The first wavelength of light will activate the first polymerization initiator causing free-radical polymerization. The desired degree and depth of polymerization at each point in the array of beams of actinic radiation is defined by the pre-programmed script and wavelength of the actinic radiation as it may interact lightly or heavily with the spectral absorption of the reactive monomer mixture in a manner consistent with Beer's law. A first functional moiety linked to the first polymerization initiator is incorporated into the polymer chain of the selectively polymerized reactive monomer mixture. After exposure to the actinic radiation, the mold assembly may be exposed to a second energy, again, not substantially activating the first photo-initiator, preferably thermal energy. To accomplish this the mold assembly shown in FIG. 3 may simply be placed in a thermally controlled environment, such as an oven, until the reactive monomer mixture is cured, for example at approximately 90 degrees Celsius for approximately two to three hours.

As an alternative, following exposure to a first actinic radiation the mold halves and exposure jig assembly are placed in the thermal apparatus for about 20 minutes to allow sufficient gelling of the reactive monomer mixture to prevent unwanted relative movement of the BC mold relative to the FC mold, at which time it is removed from the thermal apparatus and the exposure jigs removed from the mold halves. The mold halves are then immediately placed back in the thermal apparatus for the duration of the time for final cure. This allows the exposure jig to be reused if desired, during the remainder of the final lens curing step. The formed lens object can then be removed from the mold halves 202 and 203 and undergo an extraction process to remove unreacted first polymerization initiator. The extraction process to remove unreacted first polymerization initiator may be complete or incomplete. In some cases, removal of all unreacted first polymerization initiator is not required to create the desired features or optical effects. In other cases, the extraction process removes only a portion of the unreacted first initiator, enabling an optional irradiation step using a lower concentration of the first polymerization initiator. Or the extraction process can remove substantially all of the unreacted first initiator. After removing unreacted first polymerization initiator, the standard post-processing steps of lens extraction to remove other reactive monomer components and of lens hydration can be carried out to form the final ophthalmic lens. In some instances, the standard post-processing steps of lens extraction and hydration, using aqueous alcohols, water, and buffers can also extract unreacted first polymerization initiators, thereby combining two or more extraction steps into one operation. The resulting lens object will have varying properties spatially incorporated therein as determined by the different curing methods applied to the respective portions. The first wavelength, and its intensity and pattern, is selectively chosen to interact with the spectral absorbance of the reactive monomer mixture such that a desired two-dimensional or three-dimensional incorporation is achieved via Beer's law effects, as is described in detail in the '505 patent.

The method described herein permits the incorporation of functional chemistry into the lens that can change refractive properties within the lens. Variations in refractive properties can be used to impart images or other visual features into the lens or to impart features that affect visual function, for example for the purpose of generating bifocal or multifocal lenses.

While voxel-based lithography as described above is a preferred technique for the selective activation of the first polymerization initiator (compound of formula I), other techniques may also be utilized. For example, selective activation may be provided by photo masking, from the first wavelength, those areas of the reactive monomer mixture where polymerization is not desired. The non-masked areas of the reactive monomer mixture may then undergo activation and selective polymerization. The photo masks may be binary in nature, but more preferably are gray scaled. Specification, and fabrication of photo masks of this nature are known to those in the art of gray scale photolithography.

Preferably, the reactive monomer mixture has sufficient viscosity so that the polymerized moieties to do not undesirably diffuse during or immediately after the first selective polymerization described above. Various options are available for providing such viscosity. For example, a reactive monomer mixture that contains viscous components, such as macromers or pre-polymers, may be used. Diluents may also be excluded, or at least used in low concentration, to avoid significantly reducing the reactive monomer mixture's viscosity.

A preferred approach is to conduct a limited pre-cure of the reactive monomer mixture through a brief activation of the second polymerization initiator, prior to or concurrently with the first activation. Thus, for example, if the second polymerization initiator is a thermal initiator, the reactive monomer mixture in the mold assembly may be heated to briefly activate the thermal initiator and therefore initiate some polymerization of the reactive monomer mixture. The initiation and polymerization can then be halted once a desired viscosity has been achieved. By way of illustration, if the thermal initiator is AIBN, such pre-cure may be achieved by heating the reactive monomer mixture to a temperature ranging, for instance, from 40 to 150 degrees for about 0.1 to 120 minutes. Preferably, the pre-cure step is carried out prior to the selective activation of the first polymerization initiator.

According to the method, a full cure of the reactive monomer mixture is conducted following the selective polymerization. This full cure employs the second polymerization initiator present in the reactive monomer mixture. In particular, the second polymerization initiator is activated, thereby initiating the polymerization of the remaining reactive components in the reactive monomer mixture.

As noted above, the reactive monomer mixture of the method contains a monomer suitable for making the desired ophthalmic lens. By way of example, the reactive monomer mixture may comprise one or more of: hydrophilic components, hydrophobic components, silicone-containing components, wetting agents such as polyamides, crosslinking agents, and further components such as diluents and initiators.

Hydrophilic Components

Examples of suitable families of hydrophilic monomers that may be present in the reactive monomer mixture include (meth)acrylates, styrenes, vinyl ethers, (meth)acrylamides, N-vinyl lactams, N-vinyl amides, N-vinyl imides, N-vinyl ureas, O-vinyl carbamates, O-vinyl carbonates, other hydrophilic vinyl compounds, and mixtures thereof.

Non-limiting examples of hydrophilic (meth)acrylate and (meth)acrylamide monomers include: acrylamide, N-isopropyl acrylamide, N,N-dimethylaminopropyl (meth)acrylamide, N,N-dimethyl acrylamide (DMA), 2-hydroxyethyl methacrylate (HEMA), 2-hydroxypropyl (meth)acrylate, 3-hydroxypropyl (meth)acrylate, 2,3-dihydroxypropyl (meth)acrylate, 2-hydroxybutyl (meth)acrylate, 3-hydroxybutyl (meth)acrylate, 4-hydroxybutyl (meth)acrylate, N-(2-hydroxyethyl) (meth)acrylamide, N,N-bis(2-hydroxyethyl) (meth)acrylamide, N-(2-hydroxypropyl) (meth)acrylamide, N,N-bis(2-hydroxypropyl) (meth)acrylamide, N-(3-hydroxypropyl) (meth)acrylamide, N-(2-hydroxybutyl) (meth)acrylamide, N-(3-hydroxybutyl) (meth)acrylamide, N-(4-hydroxybutyl) (meth)acrylamide, 2-aminoethyl (meth)acrylate, 3-aminopropyl (meth)acrylate, 2-aminopropyl (meth)acrylate, N-2-aminoethyl (meth)acrylamides), N-3-aminopropyl (meth)acrylamide, N-2-aminopropyl (meth)acrylamide, N,N-bis-2-aminoethyl (meth)acrylamides, N,N-bis-3-aminopropyl (meth)acrylamide), N,N-bis-2-aminopropyl (meth)acrylamide, glycerol methacrylate, polyethyleneglycol monomethacrylate, (meth)acrylic acid, vinyl acetate, acrylonitrile, and mixtures thereof.

Hydrophilic monomers may also be ionic, including anionic, cationic, zwitterions, betaines, and mixtures thereof. Non-limiting examples of such charged monomers include (meth)acrylic acid, N-[(ethenyloxy)carbonyl]-o-alanine (VINAL), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT), 1-propanaminium, N,N-dimethyl-N-[3-[(1-oxo-2-propen-1-yl) amino]propyl]-3-sulfo-, inner salt (SBT), 3,5-Dioxa-8-aza-4-phosphaundec-10-en-1-aminium, 4-hydroxy-N,N,N-trimethyl-9-oxo-, inner salt, 4-oxide (9CI) (PBT), 2-methacryloyloxyethyl phosphorylcholine, 3-(dimethyl(4-vinylbenzyl)ammonio)propane-1-sulfonate (DMVBAPS), 3-((3-acrylamidopropyl)dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), and methacryloyloxy)propyl) dimethylammonio)propane-1-sulfonate (MAPDAPS).

Non-limiting examples of hydrophilic N-vinyl lactam and N-vinyl amide monomers include: N-vinyl pyrrolidone (NVP), N-vinyl-2-piperidone, N-vinyl-2-caprolactam, N-vinyl-3-methyl-2-caprolactam, N-vinyl-3-methyl-2-piperidone, N-vinyl-4-methyl-2-piperidone, N-vinyl-4-methyl-2-caprolactam, N-vinyl-3-ethyl-2-pyrrolidone, N-vinyl-4,5-dimethyl-2-pyrrolidone, N-vinyl acetamide (NVA), N-vinyl- N-methylacetamide (VMA), N-vinyl-N-ethyl acetamide, N-vinyl-N-ethyl formamide, N-vinyl formamide, N-vinyl-N-methylpropionamide, N-vinyl-N-methyl-2-methylpropionamide, N-vinyl-2-methylpropionamide, N-vinyl-N,N'-dimethylurea, 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-N-propyl-3-methylene-2-pyrrolidone, 1-N-propyl-5-methylene-2-pyrrolidone, 1-isopropyl-3-methylene-2-pyrrolidone, 1-isopropyl-5-methylene-2-pyrrolidone, N-vinyl-N-ethyl acetamide, N-vinyl-N-ethyl formamide, N-vinyl formamide, N-vinyl isopropylamide, N-vinyl caprolactam, N-vinylimidazole, and mixtures thereof Non-limiting examples of hydrophilic O-vinyl carbamates and O-vinyl carbonates monomers include N-2-hydroxyethyl vinyl carbamate and N-carboxy-β-alanine N-vinyl ester. Further examples of hydrophilic vinyl carbonate or vinyl carbamate monomers are disclosed in U.S. Pat. No. 5,070,215. Hydrophilic oxazolone monomers are disclosed in U.S. Pat. No. 4,910,277.

Other hydrophilic vinyl compounds include ethylene glycol vinyl ether (EGVE), di(ethylene glycol) vinyl ether (DEGVE), allyl alcohol, and 2-ethyl oxazoline.

The hydrophilic monomers may also be macromers or prepolymers of linear or branched poly(ethylene glycol), poly(propylene glycol), or statistically random or block copolymers of ethylene oxide and propylene oxide, having polymerizable moieties such as (meth)acrylates, styrenes, vinyl ethers, (meth)acrylamides, N-vinylamides, and the like. The macromers of these polyethers have one polymerizable group; the prepolymers may have two or more polymerizable groups.

The preferred hydrophilic monomers of the present invention are DMA, NVP, HEMA, VMA, NVA, and mixtures thereof. Preferred hydrophilic monomers include mixtures of DMA and HEMA. Other suitable hydrophilic monomers will be apparent to one skilled in the art.

Generally, there are no particular restrictions with respect to the amount of the hydrophilic monomer present in the reactive monomer mixture. The amount of the hydrophilic monomers may be selected based upon the desired characteristics of the resulting hydrogel, including water content, clarity, wettability, protein uptake, and the like. Wettability may be measured by contact angle, and desirable contact angles are less than about 100°, less than about 80°, and less than about 60°. The hydrophilic monomer may be present in an amount in the range of, for instance, about 0.1 to about 100 weight percent, alternatively in the range of about 1 to about 80 weight percent, alternatively about 5 to about 65 weight percent, alternatively in the range of about 40 to about 60 weight percent, or alternatively about 55 to about 60 weight percent, based on the total weight of the reactive components in the reactive monomer mixture.

Silicone-Containing Components

Silicone-containing components suitable for use in the reactive monomer mixture of the invention comprise one or more polymerizable compounds, where each compound independently comprises at least one polymerizable group, at least one siloxane group, and one or more linking groups connecting the polymerizable group(s) to the siloxane group(s). The silicone-containing components may, for instance, contain from 1 to 220 siloxane repeat units, such as the groups defined below. The silicone-containing component may also contain at least one fluorine atom.

The silicone-containing component may comprise: one or more polymerizable groups as defined above; one or more optionally repeating siloxane units; and one or more linking groups connecting the polymerizable groups to the siloxane units. The silicone-containing component may comprise: one or more polymerizable groups that are independently a (meth)acrylate, a styryl, a vinyl ether, a (meth)acrylamide, an N-vinyl lactam, an N-vinylamide, an O-vinylcarbamate, an O-vinylcarbonate, a vinyl group, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, an N-vinyl lactam, an N-vinylamide, a styryl, or mixtures of the foregoing; one or more optionally repeating siloxane units; and one or more linking groups connecting the polymerizable groups to the siloxane units.

The silicone-containing component may comprise: one or more polymerizable groups that are independently a (meth)acrylate, a (meth)acrylamide, or mixtures of the foregoing; one or more optionally repeating siloxane units; and one or more linking groups connecting the polymerizable groups to the siloxane units.

The silicone-containing component may comprise one or more polymerizable compounds of Formula A:

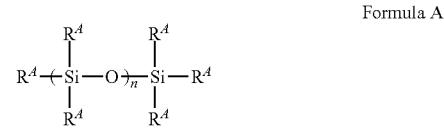

Formula A wherein:
at least one $R^A$ is a group of formula $R_g$-L- wherein $R_g$ is a polymerizable group and L is a linking group, and the remaining $R^A$ are each independently:
(a) $R_g$-L-,
(b) $C_1$-$C_{16}$ alkyl optionally substituted with one or more hydroxy, amino, amido, oxa, carboxy, alkyl carboxy, carbonyl, alkoxy, amido, carbamate, carbonate, halo, phenyl, benzyl, or combinations thereof,
(c) $C_3$-$C_{12}$ cycloalkyl optionally substituted with one or more alkyl, hydroxy, amino, amido, oxa, carbonyl, alkoxy, amido, carbamate, carbonate, halo, phenyl, benzyl, or combinations thereof,
(d) a $C_6$-$C_{14}$ aryl group optionally substituted with one or more alkyl, hydroxy, amino, amido, oxa, carboxy, alkyl carboxy, carbonyl, alkoxy, amido, carbamate, carbonate, halo, phenyl, benzyl, or combinations thereof,
(e) halo,
(f) alkoxy, cyclic alkoxy, or aryloxy,
(g) siloxy,
(h) alkyleneoxy-alkyl or alkoxy-alkyleneoxy-alkyl, such as polyethyleneoxyalkyl, polypropyleneoxyalkyl, or poly(ethyleneoxy-co-propyleneoxyalkyl), or
(i) a monovalent siloxane chain comprising from 1 to 100 siloxane repeat units optionally substituted with alkyl, alkoxy, hydroxy, amino, oxa, carboxy, alkyl carboxy, alkoxy, amido, carbamate, halo or combinations thereof; and n is from 0 to 500 or from 0 to 200, or from 0 to 100, or from 0 to 20, where it is understood that when n is other than 0, n is a distribution having a mode equal to a stated value. When n is 2 or more, the SiO units may carry the same or different $R^A$ substituents and if different $R^A$ substituents are present, the n groups may be in random or block configuration.

In Formula A, three $R^A$ may each comprise a polymerizable group, alternatively two $R^A$ may each comprise a polymerizable group, or alternatively one R may comprise a polymerizable group.

Examples of silicone-containing components suitable for use in the invention include, but are not limited to, compounds listed in Table B. Where the compounds in Table B contain polysiloxane groups, the number of SiO repeat units in such compounds, unless otherwise indicated, is preferably from 3 to 100, more preferably from 3 to 40, or still more preferably from 3 to 20.

TABLE B

| | |
|---|---|
| 1 | mono-methacryloxypropyl terminated mono-n-butyl terminated poly dimethyl siloxanes (mPDMS) (preferably containing from 3 to 15 SiO repeating units) |
| 2 | mono-acryloxypropyl terminated mono-n-butyl terminated polydimethylsiloxane |
| 3 | mono(meth)acryloxypropyl terminated mono-n-methyl terminated polydimethylsiloxane |
| 4 | mono(meth)acryloxypropyl terminated mono-n-butyl terminated polydiethylsiloxane |
| 5 | mono(meth)acryloxypropyl terminated mono-n-methyl terminated polydiethylsiloxane |
| 6 | mono(meth)acrylamidoalkylpolydialkylsiloxanes |
| 7 | mono(meth)acryloxyalkyl terminated mono-alkyl polydiarylsiloxanes |
| 8 | 3-methacryloxypropyltris(trimethylsiloxy)silane (TRIS) |
| 9 | 3-methacryloxypropylbis(trimethylsiloxy)methylsilane |
| 10 | 3-methacryloxypropylpentamethyl disiloxane |
| 11 | mono(meth)acrylamidoalkylpolydialkylsiloxanes |
| 12 | mono(meth)acrylamidoalkyl polydimethylsiloxanes |
| 13 | N-(2,3-dihydroxypropane)-N'-(propyl tetra(dimethylsiloxy) dimethylbutylsilane)acrylamide |
| 14 | N-[3-tris(trimethylsiloxy)silyl]-propyl acrylamide (TRIS-Am) |
| 15 | 2-hydroxy-3-[3-methyl-3,3-di(trimethylsiloxy)silylpropoxy]-propyl methacrylate (SiMAA) |
| 16 | 2-hydroxy-3-methacryloxypropyloxypropyl-tris(trimethylsiloxy)silane |
| 17 | 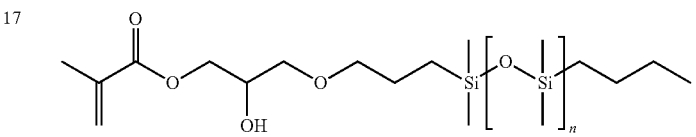 mono-(2-hydroxy-3-methacryloxypropyloxy)-propyl terminated mono-n-butyl terminated polydimethylsiloxanes (OH-mPDMS) (containing from 4 to 30, or from 4 to 20, or from 4 to 15 SiO repeat units) |
| 18 | 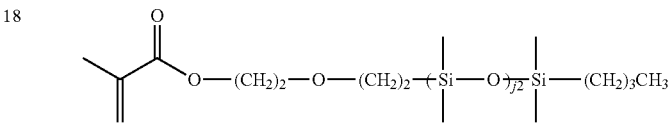 |
| 19 | 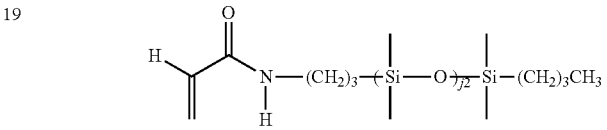 |
| 20 | 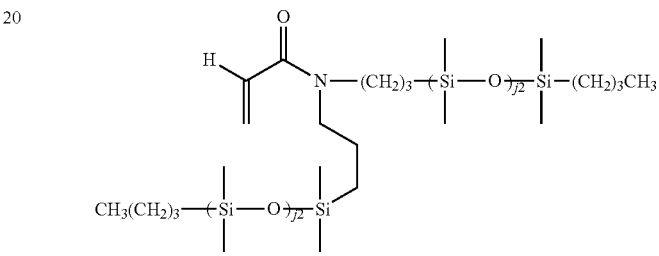 |

TABLE B-continued

21 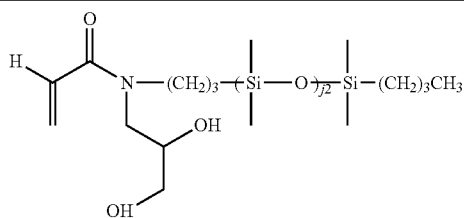

22

23

24 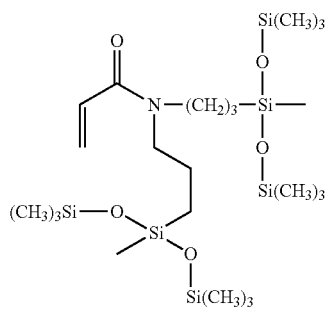

Additional non-limiting examples of suitable silicone-containing components are listed in Table C. Unless otherwise indicated, j2 where applicable is preferably from 1 to 100, more preferably from 3 to 40, or still more preferably from 3 to 15. In compounds containing j1 and j2, the sum of j1 and j2 is preferably from 2 to 100, more preferably from 3 to 40, or still more preferably from 3 to 15.

TABLE C

25

26

$p$ is 1 to 10

TABLE C-continued

| | |
|---|---|
| 27 | 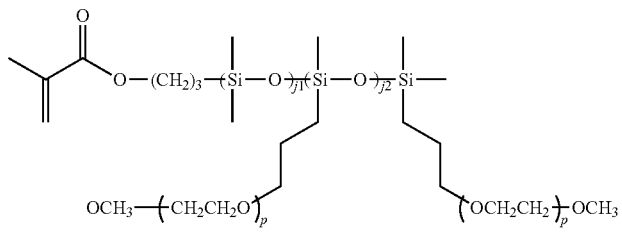<br>p is 5-10 |
| 28 | 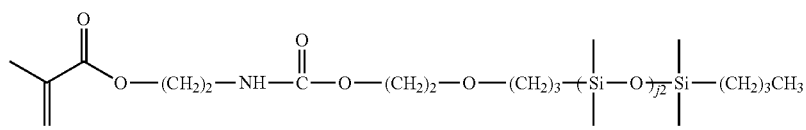 |
| 29 | 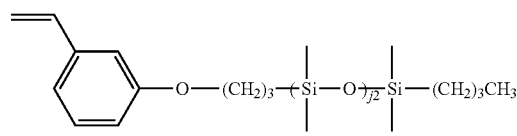 |
| 30 | 1,3-bis[4-(vinyloxycarbonyloxy)but-1-yl]tetramethyl-disiloxane |
| 31 | 3-(vinyloxycarbonylthio) propyl-[tris (trimethylsiloxy)silane] |
| 32 | 3-[tris(trimethylsiloxy)silyl] propyl allyl carbamate |
| 33 | 3-[tris(trimethylsiloxy)silyl] propyl vinyl carbamate |
| 34 | tris(trimethylsiloxy)silylstyrene (Styryl-TRIS) |
| 35 | 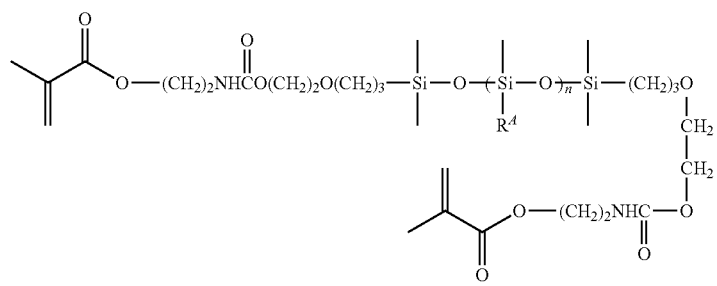<br>$R^A$ = $CH_3$ (a) or $CH_2CH_2CF_3$ (b) or $CH_2—(CH_2)_2$—$[OCH_2CH_2]_{1-10}$—$OCH_3$ (c); a + b + c = n |
| 36 | 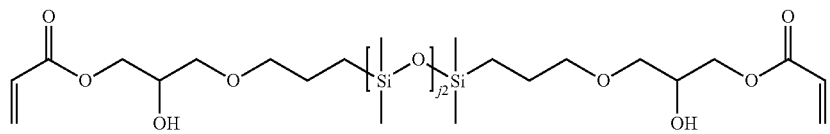 |
| 37 | 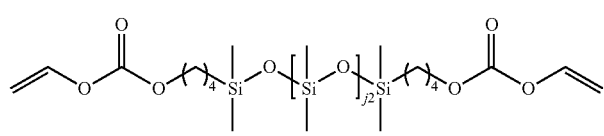 |
| 38 | 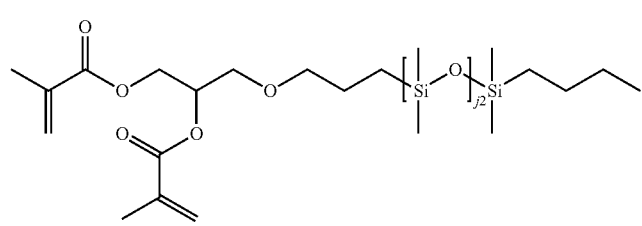 |

TABLE C-continued

39
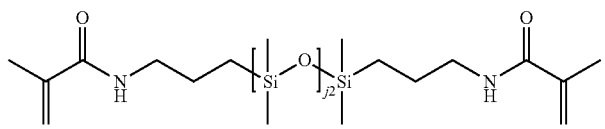

40
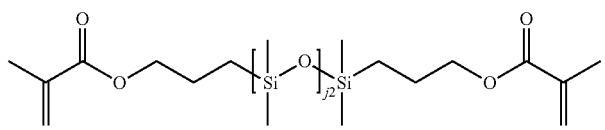

41
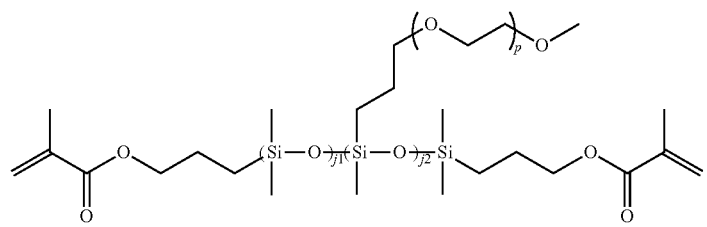

j1 = 80-90
j2 = 5-6
p = 7-8

42
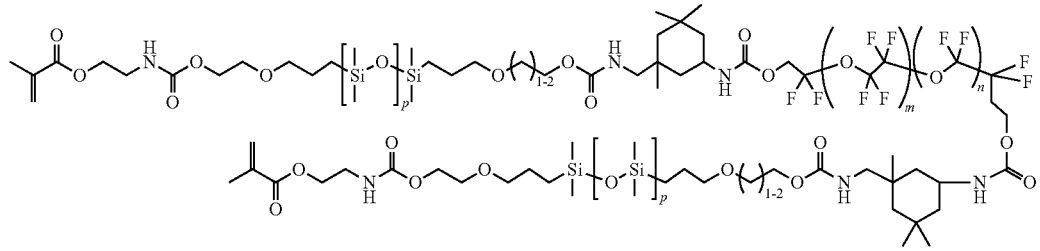

m ≈ 3.5-5.5; n ≈ 4-6.5; p ≈ 22-26

43
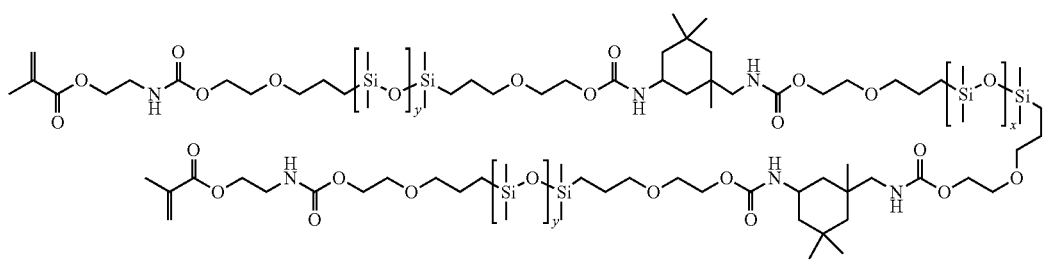

IEM-PDMS(Mn ≈ 3000)-IPDI-PDMS(Mn ≈ 2000)-IPDI-PDMS(Mn ≈ 3000)-IEM (see WO2016100457)

Mixtures of silicone-containing components may be used. By way of example, suitable mixtures may include, but are not limited to: a mixture of mono-(2-hydroxy-3-methacryloxypropyloxy)-propyl terminated mono-n-butyl terminated polydimethylsiloxane (OH-mPDMS) having different molecular weights, such as a mixture of OH-mPDMS containing 4 and 15 SiO repeat units; a mixture of OH-mPDMS with different molecular weights (e.g., containing 4 and 15 repeat SiO repeat units) together with a silicone based crosslinker, such as bis-3-acryloxy-2-hydroxypropyloxypropyl polydimethylsiloxane (ac-PDMS); a mixture of 2-hydroxy-3-[3-methyl-3,3-di(trimethylsiloxy)silylpropoxy]-propyl methacrylate (SiMAA) and mono-methacryloxypropyl terminated mono-n-butyl terminated polydimethylsiloxane (mPDMS), such as mPDMS 1000.

Silicone-containing components for use in the invention may have an average molecular weight of from about 400 to about 4000 daltons.

The silicone containing component(s) may be present in amounts up to about 95 weight %, or from about 10 to about 80 weight %, or from about 20 to about 70 weight %, based upon all reactive components of the reactive monomer mixture (excluding diluents).

Polyamides

The reactive monomer mixture may include at least one polyamide. As used herein, the term "polyamide" refers to polymers and copolymers comprising repeating units containing amide groups. The polyamide may comprise cyclic amide groups, acyclic amide groups and combinations thereof and may be any polyamide known to those of skill in the art. Acyclic polyamides comprise pendant acyclic amide groups and are capable of association with hydroxyl groups. Cyclic polyamides comprise cyclic amide groups and are capable of association with hydroxyl groups.

Examples of suitable acyclic polyamides include polymers and copolymers comprising repeating units of Formulae G1 and G2:

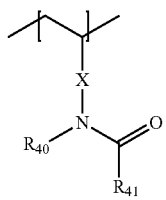

Formula G1

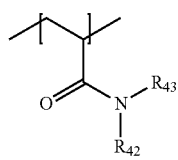

Formula G2 wherein X is a direct bond, —(CO)—, or —(CONHR$_{44}$)—, wherein R$_{44}$ is a C$_1$ to C$_3$ alkyl group; R$_{40}$ is selected from H, straight or branched, substituted or unsubstituted C$_1$ to C$_4$ alkyl groups; R$_{41}$ is selected from H, straight or branched, substituted or unsubstituted C$_1$ to C$_4$ alkyl groups, amino groups having up to two carbon atoms, amide groups having up to four carbon atoms, and alkoxy groups having up to two carbon groups; R$_{42}$ is selected from H, straight or branched, substituted or unsubstituted C$_1$ to C$_4$ alkyl groups; or methyl, ethoxy, hydroxyethyl, and hydroxymethyl; R$_{43}$ is selected from H, straight or branched, substituted or unsubstituted C$_1$ to C$_4$ alkyl groups; or methyl, ethoxy, hydroxyethyl, and hydroxymethyl; wherein the number of carbon atoms in R$_{40}$ and R$_{41}$ taken together is 8 or less, including 7, 6, 5, 4, 3, or less; and wherein the number of carbon atoms in R$_{42}$ and R$_{43}$ taken together is 8 or less, including 7, 6, 5, 4, 3, or less. The number of carbon atoms in R$_{40}$ and R$^{41}$ taken together may be 6 or less or 4 or less. The number of carbon atoms in R$_{42}$ and R$_{43}$ taken together may be 6 or less. As used herein substituted alkyl groups include alkyl groups substituted with an amine, amide, ether, hydroxyl, carbonyl or carboxy groups or combinations thereof.

R$_{40}$ and R$^{41}$ may be independently selected from H, substituted or unsubstituted C$_1$ to C$_2$ alkyl groups. X may be a direct bond, and R$_{40}$ and R$^{41}$ may be independently selected from H, substituted or unsubstituted C$_1$ to C$_2$ alkyl groups. R$_{42}$ and R$_{43}$ can be independently selected from H, substituted or unsubstituted C$_1$ to C$_2$ alkyl groups, methyl, ethoxy, hydroxyethyl, and hydroxymethyl.

The acyclic polyamides of the present invention may comprise a majority of the repeating units of Formula LV or Formula LVI, or the acyclic polyamides can comprise at least 50 mole percent of the repeating unit of Formula G or Formula G1, including at least 70 mole percent, and at least 80 mole percent. Specific examples of repeating units of Formula G and Formula G1 include repeating units derived from N-vinyl-N-methylacetamide, N-vinylacetamide, N-vinyl-N-methylpropionamide, N-vinyl-N-methyl-2-methylpropionamide, N-vinyl-2-methylpropionamide, N-vinyl-N,N'-dimethylurea, N,N-dimethylacrylamide, methacrylamide, and acyclic amides of Formulae G2 and G3:

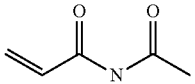

Formula G2

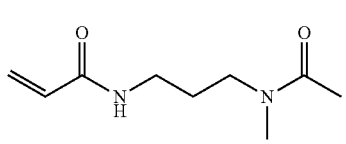

Formula G3

Examples of suitable cyclic amides that can be used to form the cyclic polyamides of include α-lactam, β-lactam, γ-lactam, δ-lactam, and ε-lactam. Examples of suitable cyclic polyamides include polymers and copolymers comprising repeating units of Formula G4:

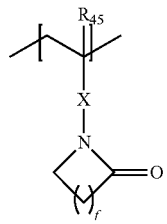

Formula G4 wherein R$_{45}$ is a hydrogen atom or methyl group; wherein f is a number from 1 to 10; wherein X is a direct bond, —(CO)—, or —(CONHR$_{46}$)—, wherein R$_{46}$ is a C$_1$ to C$_3$ alkyl group. In Formula LIX, f may be 8 or less, including 7, 6, 5, 4, 3, 2, or 1. In Formula G4, f may be 6 or less, including 5, 4, 3, 2, or 1. In Formula G4, f may be from 2 to 8, including 2, 3, 4, 5, 6, 7, or 8. In Formula LIX, f may be 2 or 3. When X is a direct bond, f may be 2. In such instances, the cyclic polyamide may be polyvinylpyrrolidone (PVP).

The cyclic polyamides of the present invention may comprise 50 mole percent or more of the repeating unit of Formula G4, or the cyclic polyamides can comprise at least 50 mole percent of the repeating unit of Formula G4, including at least 70 mole percent, and at least 80 mole percent.

The polyamides may also be copolymers comprising repeating units of both cyclic and acyclic amides. Additional repeating units may be formed from monomers selected from hydroxyalkyl(meth)acrylates, alkyl(meth)acrylates, other hydrophilic monomers and siloxane substituted (meth)acrylates. Any of the monomers listed as suitable hydrophilic monomers may be used as co-monomers to form the additional repeating units. Specific examples of additional monomers which may be used to form polyamides include 2-hydroxyethyl (meth)acrylate, vinyl acetate, acrylonitrile, hydroxypropyl (meth)acrylate, methyl (meth)acrylate and hydroxybutyl (meth)acrylate, dihydroxypropyl (meth)acrylate, polyethylene glycol mono(meth)acrylate, and the like and mixtures thereof. Ionic monomers may also be included. Examples of ionic monomers include (meth)acrylic acid, N-[(ethenyloxy)carbonyl]-o-alanine (VINAL, CAS

148969-96-4), 3-acrylamidopropanoic acid (ACA1), 5-acrylamidopentanoic acid (ACA2), 3-acrylamido-3-methylbutanoic acid (AMBA), 2-(methacryloyloxy)ethyl trimethylammonium chloride (Q Salt or METAC), 2-acrylamido-2-methylpropane sulfonic acid (AMPS), 1-propanaminium, N-(2-carboxyethyl)-N,N-dimethyl-3-[(1-oxo-2-propen-1-yl)amino]-, inner salt (CBT, carboxybetaine; CAS 79704-35-1), 1-propanaminium, N,N-dimethyl-N-[3-[(1-oxo-2-propen-1-yl)amino]propyl]-3-sulfo-, inner salt (SBT, sulfobetaine, CAS 80293-60-3), 3,5-Dioxa-8-aza-4-phosphaundec-10-en-1-aminium, 4-hydroxy-N,N,N-trimethyl-9-oxo-, inner salt, 4-oxide (9CI) (PBT, phosphobetaine, CAS 163674-35-9, 2-methacryloyloxyethyl phosphorylcholine, 3-(dimethyl(4-vinylbenzyl)ammonio) propane-1-sulfonate (DMVBAPS), 3-((3-acrylamidopropyl) dimethylammonio)propane-1-sulfonate (AMPDAPS), 3-((3-methacrylamidopropyl)dimethylammonio)propane-1-sulfonate (MAMPDAPS), 3-((3-(acryloyloxy)propyl)dimethylammonio)propane-1-sulfonate (APDAPS), methacryloyloxy)propyl)dimethylammonio)propane-1-sulfonate (MAPDAPS).

The reactive monomer mixture may comprise both an acyclic polyamide and a cyclic polyamide or copolymers thereof. The acyclic polyamide can be any of those acyclic polyamides described herein or copolymers thereof, and the cyclic polyamide can be any of those cyclic polyamides described herein or copolymers thereof. The polyamide may be selected from the group polyvinylpyrrolidone (PVP), polyvinylmethyacetamide (PVMA), polydimethylacrylamide (PDMA), polyvinylacetamide (PNVA), poly(hydroxyethyl(meth)acrylamide), polyacrylamide, and copolymers and mixtures thereof. The polyamide may be a mixture of PVP (e.g., PVP K90) and PVMA (e.g., having a $M_w$ of about 570 KDa).

The total amount of all polyamides in the reactive monomer mixture may be in the range of between 1 weight percent and about 35 weight percent, including in the range of about 1 weight percent to about 15 weight percent, and in the range of about 5 weight percent to about 15 weight percent, in all cases, based on the total weight of the reactive components of the reactive monomer mixture.

Without intending to be bound by theory, when used with a silicone hydrogel, the polyamide functions as an internal wetting agent. The polyamides of the present invention may be non-polymerizable, and in this case, are incorporated into the silicone hydrogels as semi-interpenetrating networks. The polyamides are entrapped or physically retained within the silicone hydrogels. Alternatively, the polyamides of the present invention may be polymerizable, for example as polyamide macromers or prepolymers, and in this case, are covalently incorporated into the silicone hydrogels. Mixtures of polymerizable and non-polymerizable polyamides may also be used.

When the polyamides are incorporated into the reactive monomer mixture they may have a weight average molecular weight of at least 100,000 daltons; greater than about 150,000; between about 150,000 to about 2,000,000 daltons; between about 300,000 to about 1,800,000 daltons. Higher molecular weight polyamides may be used if they are compatible with the reactive monomer mixture.

Cross-Linking Agents

It is generally desirable to add one or more cross-linking agents, also referred to as cross-linking monomers, multifunctional macromers, and prepolymers, to the reactive monomer mixture. The cross-linking agents may be selected from bifunctional crosslinkers, trifunctional crosslinkers, tetrafunctional crosslinkers, and mixtures thereof, including silicone-containing and non-silicone containing cross-linking agents. Non-silicone-containing cross-linking agents include ethylene glycol dimethacrylate (EGDMA), tetraethylene glycol dimethacrylate (TEGDMA), trimethylolpropane trimethacrylate (TMPTMA), triallyl cyanurate (TAC), glycerol trimethacrylate, methacryloxyethyl vinylcarbonate (HEMAVc), allylmethacrylate, methylene bisacrylamide (MBA), and polyethylene glycol dimethacrylate wherein the polyethylene glycol has a molecular weight up to about 5000 Daltons. The cross-linking agents are used in the usual amounts, e.g., from about 0.000415 to about 0.0156 mole per 100 grams of reactive Formulas in the reactive monomer mixture. Alternatively, if the hydrophilic monomers and/or the silicone-containing components are multifunctional by molecular design or because of impurities, the addition of a cross-linking agent to the reactive monomer mixture is optional. Examples of hydrophilic monomers and macromers which can act as the cross-linking agents and when present do not require the addition of an additional cross-linking agent to the reactive monomer mixture include (meth)acrylate and (meth)acrylamide endcapped polyethers. Other cross-linking agents will be known to one skilled in the art and may be used to make the silicone hydrogel of the present invention.

It may be desirable to select crosslinking agents with similar reactivity to one or more of the other reactive components in the formulation. In some cases, it may be desirable to select a mixture of crosslinking agents with different reactivity in order to control some physical, mechanical or biological property of the resulting silicone hydrogel. The structure and morphology of the silicone hydrogel may also be influenced by the diluent(s) and cure conditions used.

Multifunctional silicone-containing components, including macromers, cross-linking agents, and prepolymers, may also be included to further increase the modulus and retain tensile strength. The silicone containing cross-linking agents may be used alone or in combination with other cross-linking agents. An example of a silicone containing component which can act as a cross-linking agent and, when present, does not require the addition of a crosslinking monomer to the reactive monomer mixture includes α,ω-bismethacryloxypropyl polydimethylsiloxane. Another example is bis-3-acryloxy-2-hydroxypropyloxypropyl polydimethylsiloxane (ac-PDMS).

Cross-linking agents that have rigid chemical structures and polymerizable groups that undergo free radical polymerization may also be used. Non-limiting examples of suitable rigid structures include cross-linking agents comprising phenyl and benzyl ring, such are 1,4-phenylene diacrylate, 1,4-phenylene dimethacrylate, 2,2-bis(4-methacryloxyphenyl)-propane, 2,2-bis[4-(2-acryloxyethoxy)phenyl]propane, 2,2-bis[4-(2-hydroxy-3-methacryloxypropoxy)-phenyl]propane, and 4-vinylbenzyl methacrylate, and combinations thereof. Rigid crosslinking agents may be included in amounts between about 0.5 and about 15, or 2-10, 3-7 based upon the total weight of all of the reactive components. The physical and mechanical properties of the silicone hydrogels of the present invention may be optimized for a particular use by adjusting the components in the reactive monomer mixture.

Non-limiting examples of silicone cross-linking agents also include the multi-functional silicone-containing components described in Table D above.

Further Constituents

The reactive monomer mixture may contain additional components such as, but not limited to, diluents, initiators, UV absorbers, visible light absorbers, photochromic compounds, pharmaceuticals, nutraceuticals, antimicrobial substances, tints, pigments, copolymerizable dyes, nonpolymerizable dyes, release agents, and combinations thereof.

Classes of suitable diluents for silicone hydrogel reactive monomer mixtures include alcohols having 2 to 20 carbon atoms, amides having 10 to 20 carbon atoms derived from primary amines and carboxylic acids having 8 to 20 carbon atoms. The diluents may be primary, secondary, and tertiary alcohols.

Generally, the reactive components are mixed in a diluent to form a reactive monomer mixture. Suitable diluents are known in the art. For silicone hydrogels, suitable diluents are disclosed in WO 03/022321 and U.S. Pat. No. 6,020,445, the disclosure of which is incorporated herein by reference.

Classes of suitable diluents for silicone hydrogel reactive monomer mixtures include alcohols having 2 to 20 carbons, amides having 10 to 20 carbon atoms derived from primary amines, and carboxylic acids having 8 to 20 carbon atoms. Primary and tertiary alcohols may be used. Preferred classes include alcohols having 5 to 20 carbons and carboxylic acids having 10 to 20 carbon atoms.

Specific diluents which may be used include 1-ethoxy-2-propanol, diisopropylaminoethanol, isopropanol, 3,7-dimethyl-3-octanol, 1-decanol, 1-dodecanol, 1-octanol, 1-pentanol, 2-pentanol, 1-hexanol, 2-hexanol, 2-octanol, 3-methyl-3-pentanol, tert-amyl alcohol, tert-butanol, 2-butanol, 1-butanol, 2-methyl-2-pentanol, 2-propanol, 1-propanol, ethanol, 2-ethyl-1-butanol, (3-acetoxy-2-hydroxypropyloxy)-propylbis(trimethylsiloxy) methylsilane, 1-tert-butoxy-2-propanol, 3,3-dimethyl-2-butanol, tert-butoxyethanol, 2-octyl-1-dodecanol, decanoic acid, octanoic acid, dodecanoic acid, 2-(diisopropylamino)ethanol mixtures thereof and the like. Examples of amide diluents include N,N-dimethyl propionamide and dimethyl acetamide.

Preferred diluents include 3,7-dimethyl-3-octanol, 1-dodecanol, 1-decanol, 1-octanol, 1-pentanol, 1-hexanol, 2-hexanol, 2-octanol, 3-methyl-3-pentanol, 2-pentanol, t-amyl alcohol, tert-butanol, 2-butanol, 1-butanol, 2-methyl-2-pentanol, 2-ethyl-1-butanol, ethanol, 3,3-dimethyl-2-butanol, 2-octyl-1-dodecanol, decanoic acid, octanoic acid, dodecanoic acid, mixtures thereof and the like.

More preferred diluents include 3,7-dimethyl-3-octanol, 1-dodecanol, 1-decanol, 1-octanol, 1-pentanol, 1-hexanol, 2-hexanol, 2-octanol, 1-dodecanol, 3-methyl-3-pentanol, 1-pentanol, 2-pentanol, t-amyl alcohol, tert-butanol, 2-butanol, 1-butanol, 2-methyl-2-pentanol, 2-ethyl-1-butanol, 3,3-dimethyl-2-butanol, 2-octyl-1-dodecanol, mixtures thereof and the like. If a diluent is present, generally there are no particular restrictions with respect to the amount of diluent present. When diluent is used, the diluent may be present in an amount in the range of about 2 to about 70 weight percent, including in the range of about 5 to about 50 weight percent, and in the range of about 15 to about 40 weight percent, based on the total weight of the reactive monomer mixtures (including reactive and nonreactive Formulas). Mixtures of diluents may be used.

The reactive monomer mixture for making the ophthalmic lenses of the invention may comprise, in addition to a first polymerization initiator and a second polymerization initiator, any of the polymerizable compounds and optional components described above.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, and a hydrophilic component selected from DMA, NVP, HEMA, VMA, NVA, methacrylic acid, and mixtures thereof. Preferred are mixtures of HEMA and methacrylic acid.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component, and a silicone-containing component.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component selected from DMA, HEMA and mixtures thereof, a silicone-containing component selected from 2-hydroxy-3-[3-methyl-3,3-di(trimethylsiloxy)silylpropoxy]-propyl methacrylate (SiMAA), mono-methacryloxypropyl terminated mono-n-butyl terminated polydimethylsiloxane (mPDMS), mono-(2-hydroxy-3-methacryloxypropyl)-propyl ether terminated mono-n-butyl terminated polydimethylsiloxane (OH-mPDMS), and mixtures thereof, and a wetting agent (preferably PVP or PVMA). For the hydrophilic component, mixtures of DMA and HEMA are preferred. For the silicone containing component, mixtures of SiMAA and mPDMS are preferred.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component comprising a mixture of DMA and HEMA; a silicone-containing component comprising a mixture of OH-mPDMS having from 2 to 20 repeat units (preferably a mixture of 4 and 15 repeat units). Preferably, the reactive monomer mixture further comprises a silicone-containing crosslinker, such as ac-PDMS. Also preferably, the reactive monomer mixture contains a wetting agent (preferably DMA, PVP, PVMA or mixtures thereof).

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component; between about 1 and about 15 wt % at least one polyamide (e.g., an acyclic polyamide, a cyclic polyamide, or mixtures thereof); at least one first mono-functional, hydroxyl substituted poly(disubstituted siloxane) having 4 to 8 siloxane repeating units (e.g., OH-mPDMS where n is 4 to 8, preferably n is 4); at least one second hydroxyl substituted poly(disubstituted siloxane) that is a mono-functional hydroxyl substituted poly(disubstituted siloxane)s having 10 to 200 or 10-100 or 10-50 or 10-20 siloxane repeating units (e.g., OH-mPDMS where n is 10 to 200 or 10-100 or 10-50 or 10-20, preferably n is 15); about 5 to about 35 wt % of at least one hydrophilic monomer; and optionally a multifunctional hydroxyl substituted poly(disubstituted siloxane)s having 10 to 200, or 10 to 100 siloxane repeating units (e.g., ac-PDMS). Preferably, the first monofunctional, hydroxyl substituted poly(disubstituted siloxane) and the second hydroxyl substituted poly(disubstituted siloxane) are present in concentrations to provide a ratio of weight percent of the first mono-functional, hydroxyl substituted poly(disubstituted siloxane) to weight percent of the second hydroxyl substituted poly(disubstituted siloxane) of 0.4-1.3, or 0.4-1.0.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component such as DMA; a silicone-containing component such as compound 8 in Table B ((TRIS), and a silicone macromer, such as compound 42 in Table C.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component such as DMA and/or NVP; a silicone-containing component such as compound 14 in Table B ((TRIS-Am), and a silicone macromer, such as compound 43 in Table C (IEM-PDMS-IPDI-PDMS-IPDI-PDMS-IEM).

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component such as VMA; and a silicone macromer, such as compound 35 in Table C.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component such as VMA and/or NVP; a silicone-containing component such as compound 28 in Table C (e.g., where j2 is about 16), a silicone macromer, such as compound 35 in Table C.

The reactive monomer mixture may comprise: a first polymerization initiator having a first functional moiety chemically linked to it (i.e., a compound of formula I), a second polymerization initiator that is capable of being activated by a second activation that does not substantially activate the first polymerization initiator, and a hydrophilic component, a hydrophilic component such as VMA and/or NVP; a silicone-containing component such as a compound 18 in Table B (e.g., where j2 is about 4), a silicone macromer, such as a compound 41 in Table C.

The foregoing reactive monomer mixtures may contain optional ingredients such as, but not limited to, internal wetting agents, crosslinkers, other UV or HEV absorbers, and diluents. Moreover, the ophthalmic lenses made from the foregoing reactive monomer mixtures may undergo further treatment including, but not limited to, plasma treatment, application of a coating (such as in-package coatings (IPCs) as described in U.S. Pat. No. 8,480,227), and the like.

The formed lens object can then be removed from the mold halves by mechanical means, solvent swelling, or combinations thereof, and then undergo an extraction process to remove unreacted first polymerization initiator. The extraction process to remove unreacted first polymerization initiator may be complete or incomplete. In some cases, removal of all unreacted first polymerization initiator is not required to create the desired features or optical effects. In other cases, the extraction process removes only a portion of the unreacted first initiator, enabling an optional irradiation step using a lower concentration of the first polymerization initiator. Or the extraction process can remove substantially all of the unreacted first initiator. After removing unreacted first polymerization initiator, the standard post-processing steps of lens extraction to remove other reactive monomer components and of lens hydration can be carried out to form the final ophthalmic lens. In some instances, the standard post-processing steps of lens extraction and hydration, using aqueous alcohols, water, and buffers can also extract unreacted first polymerization initiators, thereby combining two or more extraction steps into one operation.

Aqueous solutions are solutions which comprise water. The aqueous solutions of the present invention may comprise at least about 20 weight percent water, or at least about 50 weight percent water, or at least about 70 weight percent water, or at least about 95 weight percent water. Aqueous solutions may also include additional water soluble Formulas such as inorganic salts or release agents, wetting agents, slip agents, pharmaceutical and nutraceutical Formulas, combinations thereof and the like. Release agents are compounds or mixtures of compounds which, when combined with water, decrease the time required to release a contact lens from a mold, as compared to the time required to release such a lens using an aqueous solution that does not comprise the release agent. The aqueous solutions may not require special handling, such as purification, recycling or special disposal procedures.

Extraction may be accomplished, for example, via immersion of the lens in an aqueous solution or exposing the lens to a flow of an aqueous solution. Extraction may also include, for example, one or more of: heating the aqueous solution; stirring the aqueous solution; increasing the level of release aid in the aqueous solution to a level sufficient to cause release of the lens; mechanical or ultrasonic agitation of the lens; and incorporating at least one leaching or extraction aid in the aqueous solution to a level sufficient to facilitate adequate removal of unreacted components from the lens. The foregoing may be conducted in batch or continuous processes, with or without the addition of heat, agitation or both.

Application of physical agitation may be desired to facilitate leach and release. For example, the lens mold part to which a lens is adhered can be vibrated or caused to move back and forth within an aqueous solution. Other methods may include ultrasonic waves through the aqueous solution.

The lenses may be sterilized by known means such as, but not limited to, autoclaving.

As indicated above, preferred ophthalmic lenses are contact lenses, more preferably soft hydrogel contact lenses. Silicone hydrogel ophthalmic lenses (e.g., contact lenses) that may be prepared according to the invention preferably exhibit the following properties. All values are prefaced by "about," and the lenses may have any combination of the listed properties. The properties may be determined by methods known to those skilled in the art, for instance as described in United States pre-grant publication US20180037690, which is incorporated herein by reference.

Water concentration %: at least 20%, or at least 25% and up to 80% or up to 70%

Haze: 30% or less, or 10% or less

Advancing dynamic contact angle (Wilhelmy plate method): 100° or less, or 800 or less; or 50° or less Tensile Modulus (psi): 120 or less, or 80 to 120

Oxygen permeability (Dk, barrers): at least 80, or at least 100, or at least 150, or at least 200

Elongation to Break: at least 100

For ionic silicon hydrogels, the following properties may also be preferred (in addition to those recited above):

Lysozyme uptake (μg/lens): at least 100, or at least 150, or at least 500, or at least 700

Polyquaternium 1 (PQ1) uptake (%): 15 or less, or 10 or less, or 5 or less

Some embodiments of the invention will now be described in detail in the following Examples.

EXAMPLES

The following abbreviations will be used throughout the Examples and Figures and have the following meanings:

DMA: N, N-dimethylacrylamide (Jarchem)
HEMA: 2-hydroxyethyl methacrylate (Bimax)
PVP K12, K30, or K90: poly(N-vinylpyrrolidone) (ISP Ashland)
TEGDMA: tetraethylene glycol dimethacrylate (Esstech)
Omnirad 819: bis(2,4,6-trimethylbenzoyl)-phenylphosphineoxide (IGM Resins)
AIBN: azobisisobutyronitrile [CAS 78-67-1]
SiMAA: 2-propenoic acid, 2-methyl-2-hydroxy-3-[3-[1, 3,3,3-tetramethyl-1-[(trimethylsilyl)oxy]disiloxanyl] propoxy]propyl ester (Toray) or 3-(3-(1,1,1,3,5,5,5-heptamethyltrisiloxan-3-yl)propoxy)-2-hydroxypropyl methacrylate
HO-mPDMS: mono-n-butyl terminated mono-(2-hydroxy-3-methacryloxypropyloxy)-propyl terminated polydimethylsiloxane ($M_n$=1400 grams/mole, n=15) (Ortec or DSM-Polymer Technology Group)

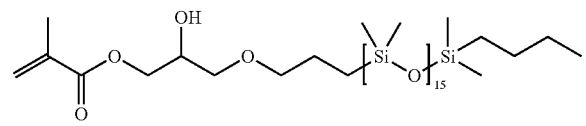

Norbloc: 2-(2'-hydroxy-5-methacrylyloxyethylphenyl)-2H-benzotriazole (Janssen)
Blue HEMA: 1-amino-4-[3-(4-(2-methacryloyloxy-ethoxy)-6-chlorotriazin-2-ylamino)-4-sulfophenylamino]anthraquinone-2-sulfonic acid, as described in U.S. Pat. No. 5,944,853
Borate Buffered Packing Solution: 18.52 grams (300 mmol) of boric acid, 3.7 grams (9.7 mmol) of sodium borate decahydrate, and 28 grams (197 mmol) of sodium sulfate were dissolved in enough deionized water to fill a 2 liter volumetric flask.
D3O: 3,7-dimethyl-3-octanol (Vigon)
HCl: hydrochloric acid
IPA: 2-propanol
ACN: acetonitrile
THF: tetrahydrofuran
PEO: polyethylene oxide
DMF: dimethylformamide
DCM: dichloromethane
PP: polypropylene which is the homopolymer of propylene
TT: Tuftec which is a hydrogenated styrene butadiene block copolymer (Asahi Kasei Chemicals)
Z: Zeonor which is a polycycloolefin thermoplastic polymer (Nippon Zeon Co Ltd)
LED: light emitting diode
$^1$N NMR: proton nuclear magnetic resonance spectroscopy
UV-VIS: ultraviolet-visible spectroscopy
TLC: thin layer chromatography
ID: inner diameter
L: liter(s)
mL: milliliter(s)
mM: millimolar
M: molar
Equiv. or eq.: equivalent
kg: kilogram(s)
g: gram(s)
mg: milligram(s)
mol: mole
mmol: millimole
min: minute(s)
mm: millimeter(s)
cm: centimeter(s)
μm: micrometer(s)
nm: nanometer(s)
mW: milliwatt(s)
mJ: millijoule(s)
Pa: pascal
PSI: pounds per square inch
Abs: absorption
% T: Percent Transmission
MAPO: monoacylphosphine oxide
DMD: digital micromirror device Examples Example 1—Synthesis of Monoacyl Phosphine Oxide Mono-Terminated Poly(N-Vinyl Pyrrolidone) (MAPO-PVP) as Shown in Scheme A To a 3-neck round bottom flask fitted with a reflux condenser, N-vinyl pyrrolidone (20.0 grams), ethanol (41.0 grams) and Omnirad 819 (1.0 gram) were charged under yellow lights, degassed, and heated under nitrogen at 65° C. The reaction mixture was then irradiated using 435 nm LED lights having an intensity of about 1.22 mW/cm$^2$ for thirty minutes. The reaction mixture was quenched in air and cooled to room temperature. The solvent was removed under reduced pressure, followed by precipitation in cold diethyl ether to afford a white solid upon filtration. The white solid was suspended in diethyl ether (50 mL) and stirred for 30 minutes and re-filtered. The product ("MAPO-PVP") was then washed with diethyl ether (3×50 mL) and air dried to afford a white powder (16.0 grams, 80% yield). The polymer structure was characterized by 500 MHz $^1$H-NMR spectroscopy in deuterium oxide; see FIG. 4. The molecular weight and its distribution were determined by viscosity comparison and size exclusion multiangle light scattering (SEC-MALS) against commercially available samples of PVP K12-K90. It should be noted that the product "MAPO-PVP" is a mixture of monoacyl phosphine oxide terminated PVP and monoacyl terminated PVP as shown in Scheme A. The type of monoacyl groups depends on the type of bisacylphosphine oxide initiator used in the copolymerization; if the initiator has two different acyl groups, then the "MAPO-PVP" is a mixture of two monoacyl phosphine oxide terminated PVPs and two monoacyl terminated PVPs. It is important to protect these materials from ambient light in storage. The MAPO-PVP is an example of the first formula in Table A.

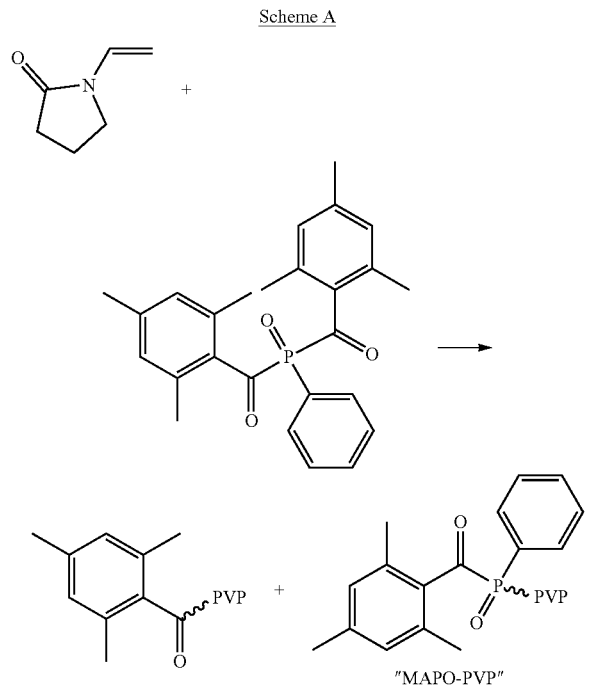

Scheme A

"MAPO-PVP"

Viscosity measurements were performed at room temperature on an Anton-Paar Rheometer using a CP50-1 cone and plate from a shear rate of 1 sec$^{-1}$ to 500 sec$^{-1}$ with a run time of 400 seconds, collecting data every 10 seconds. Measurements were done in duplicate and averaged. The viscosity results are shown in Table 1. The viscosity data indicated that MAPO-PVP exhibited a viscosity slightly greater than that of PVP K30.

TABLE 1

Viscosity Data

| Sample | Viscosity (Pa-sec) |
| --- | --- |
| PVP K12 | 0.0011176 |
| PVP K30 | 0.0012584 |
| PVP K90 | 0.0034210 |
| MAPO-PVP | 0.0014032 |

Polymer molecular weights were determined by Size Exclusion Chromatography with Multi-Angle Light Scattering (SEC-MALS) relative to molecular weights of commercially available samples of PVP K12 and PVP K30. The SEC-MALS setup employed 20% ACN in deionized water (v/v) (with 50 mM $Na_2SO_4$) as the mobile phase at a flow rate of 0.3 mL/min at 40° C. and three Tosoh Biosciences TSK-gel columns in series [SuperAW3000 4 μm, 6.0 mm ID×15 cm (PEO/DMF Exclusion Limit=60,000 grams/mole), SuperAW4000 6 μm, 6.0 mm ID×15 cm (PEO/DMF Exclusion Limit=400,000 grams/mole) and a SuperAW5000 7 μm, 6.0 mm ID×15 cm (PEO/DMF Exclusion Limit=4,000,000 grams/mole)] with an online Agilent 1200 UV/VIS diode array detector, a Wyatt Optilab rEX interferometric refractometer, and a Wyatt mini-DAWN Treos multiangle laser scattering (MALS) detector (λ=658 nm). Molecular weights and polydispersity data were calculated using the Wyatt ASTRA 6.1.1.17 SEC/LS software package. In FIG. 5, the SEC-MALS chromatograms of PVP K12, PVP K30, and MAPO-PVP are shown. Since the chromatograms of PVP K30 and MAPO-PVP were similar, it was inferred that PVP K30 and MAPO-PVP had similar molecular weight distributions.

Example 2—Synthesis of Monoacyl Phosphine Oxide Mono-Terminated Poly(N, N-Dimethylacrylamide) (MAPO-PDMA)

To a 3-neck round bottom flask fitted with a reflux condenser, N, N-dimethylacrylamide (11.0 grams), ethanol (11.0 grams) and Omnirad 819 (400 milligrams) were charged under yellow lights, degassed, and heated under nitrogen at 75° C. The reaction mixture was then irradiated using 435 nm LED lights having an intensity of about 1.22 mW/cm$^2$ for twenty minutes. The reaction was then quenched in air and cooled to room temperature followed by precipitation in cold diethyl ether to afford a white solid that was re-dissolved in methanol and precipitated with diethyl ether. This precipitation process was repeated once more to afford a white solid (65% yield). The MAPO-PDMA was characterized by 500 MHz $^1$H-NMR spectroscopy in deuterated methanol; see FIG. 6.

Polymer molecular weights were determined by Size Exclusion Chromatography with Multi-Angle Light Scattering (SEC-MALS). The SEC-MALS setup employed methanol (with 10 mM LiBr) as the mobile phase at a flow rate of 0.6 mL/min at 50° C. and three Tosoh Biosciences TSK-gel columns in series [SuperAW3000 4 μm, 6.0 mm ID×15 cm (PEO/DMF Exclusion Limit=60,000 grams/mole), SuperAW4000 6 μm, 6.0 mm ID×15 cm (PEO/DMF Exclusion Limit=400,000 grams/mole) and a SuperAW5000 7 μm, 6.0 mm ID×15 cm (PEO/DMF Exclusion Limit=4,000,000 grams/mole)] with an online Agilent 1200 UV/VIS diode array detector, a Wyatt Optilab rEX interferometric refractometer, and a Wyatt mini-DAWN Treos multiangle laser scattering (MALS) detector (λ=658 nm). A df/dc value of 0.183 mL/g at 30° C. (λ=658 nm) was used for absolute molecular weight determination. Absolute molecular weights and polydispersity data were calculated using the Wyatt ASTRA 6.1.1.17 SEC/LS software package. The number average molecular weight was determined to be 56,500 grams/mole; the weight average molecular weight was determined to be 96,100 grams/mole; resulting in a polydispersity index [$M_w/M_n$] of 1.6.

Example 3 (Prophetic)—Synthesis of Monoacyl Phosphine Oxide Mono-Terminated Poly(N-Vinyl Pyrrolidone-Co-N, N-Dimethylacrylamide)

To a 3-neck round bottom flask fitted with a reflux condenser, N-vinyl pyrrolidone (10.0 grams) N, N-dimethylacrylamide (10.0 grams), ethanol (41.0 grams) and Omnirad 819 (1.0 gram) are charged under yellow lights, degassed, and heated under nitrogen at 65° C. The reaction mixture is then irradiated using 435 nm LED lights having an intensity of about 1.22 mW/cm$^2$ for thirty minutes. The reaction mixture is quenched in air and cooled to room temperature. The solvent is removed under reduced pressure, followed by precipitation in cold diethyl ether to afford a white solid upon filtration. The white solid is suspended in diethyl ether (50 mL) and stirred for 30 minutes and re-filtered. The product ("MAPO-Poly[NVP-co-DMA]") is then washed with diethyl ether (3×50 mL) and air dried to afford a white powder.

Example 4 (Optical Path Length Modification)

A reactive monomer mixture was formed comprising the formulation listed in Table 2. The reactive monomer mixture was degassed by applying a vacuum for about 15 minutes. Then, about 100 microliters of reactive monomer mixture were dispensed into a Zeonor base curve mold thereafter a Zeonor front curve mold was placed onto base curve mold. The resulting mold assembly was transferred into the irradiation jig shown in FIG. 3 which was then connected to computer controlled light projector in which a 365 nanometer LED light source having an intensity of 47.5 mW/cm$^2$ is directed to distinct volumes within the mold cavity and is modulated by digital light processing chip or digital micromirror device.

TABLE 2

Formulation

| Component | Weight Percent |
|---|---|
| OH-mPDMS (n = 15) | 22.69% |
| SiMAA | 20.50% |
| DMA | 19.72% |
| HEMA | 5.51% |
| Blue HEMA | 0.01% |
| PVP K90 | 2.24% |
| PVP-MAPO (Ex. 1) | 7.85% |
| TEGDMA | 1.31% |
| Norbloc | 1.46% |
| AIBN | 0.25% |
| D3O (diluent) | 18.45% |
| Total | 100.00% |

The computer controlled light projector was programmed to illuminate or irradiate the USAF 1951 Test Target shown in FIG. 7. The USAF 1951 test chart is a widely known image encompassing a broad array of spatial frequencies and recognizable numerals and therefore is a good reference to objectively measure the overall quality of the imparted image profile. The reactive monomer mixture in the mold cavity was irradiated by the computer controlled light projector using a maximum energy of 700 mJ/cm$^2$ and an exposure time of 31.6 seconds to impart the USAF 1951 test chart image profile on a contact lens and then heated to 90° C. for 2 hours and 45 minutes to thermally cure the rest of the reactive monomer mixture into a contact lens. The resulting lens was released using 70% (v/v) aqueous IPA (about one hour of soaking), extracted two times with 70% (v/v) aqueous IPA for thirty minutes, hydrated with deionized water for thirty minutes, and then equilibrated with packing solution. An optical micrograph of the final hydrated lens is shown in FIG. 8. Note: the exact conditions for the computer-controlled light projector usually need to be optimized based on the composition of the reactive monomer mixture and the project image. This optimization usually involves varying the energy delivered to the reactive monomer mixture in the mold cavity [energy=LED intensity×DMID attenuation×exposure time] and the exposure time. Preferably, the optimization uses the highest intensity possible with the shortest exposure time.

To improve the spatial resolution, the above experiment was repeated with a thermal precuring step at 90° C. for 5, 10, and 15 minutes before the light projector irradiation. The precure step increases the viscosity of the reactive monomer mixture prior to the light projector irradiation, thereby improving image quality by reducing molecular motion. Based on these data, a ten-minute precure step appeared to improve imparted profile image quality and reproducibility.

Example 2 (Optical Features)

Example 1 is repeated using a ten-minute precure but instead of projecting an image, the computer controlled light projector irradiated a pattern of circular dots wherein individual dots were exposed to different energy levels and thereby created pillars of different optical paths due to the localized change in volume and refractive index after the lens has been demolded, extracted, hydrated, and equilibrated as described in example 1. In this way, a calibration curve was generated by plotting the energy applied (mJ) versus the delta optical path length effect (wavefront measurement in waves after conversion from packing solution to air) versus the wavefront value of an untreated lens of the same design for each pillar location. For energy exposures below about 100 mJ, the calibration curve was reasonably linear and deterministic. Such a relationship allows for the creation of optical features in a predictable manner, such as adding spherical power or defocus or cylindrical power to a lens that was made in a mold cavity designed only to exhibit a fixed spherical power. Based on this information, using an exposure time of 3.6 seconds and energy level of 86 mJ/cm$^2$, the computer-controlled projector irradiated a spherical power image or a cylindrical power image into the lens cavity. The projected images as well as the two-dimensional depictions of the measured delta wavefronts taken of the fully equilibrated lenses are shown in FIG. 9. The estimated change in spherical power by adding some defocus was approximately 0.7 diopters, and the estimated addition of cylindrical power was approximately 0.12 diopters.

A calibrated dual interferometric method was used for measuring contact lens parameters in packing solution. These parameters included equivalent sphere power at multiple apertures (diopters or D), cylinder power at multiple apertures (diopters or D), diameter (millimeters or mm), center thickness (millimeters or mm), sagittal height (millimeters or mm), and root mean squared (RMS) optical path wavefront deviation from lens design target in micrometers or microns (μm) and sometimes expressed in waves with sphere/cylinder power and coma removed as measured using a 6.5-millimeter aperture. The instrument consists of a custom, proprietary interferometer for the measurement of wavefront parameters and a Lumetrics OptiGauge® II low-coherence interferometer for the measurement of the dimensional parameters of sagittal height and center thickness. The two individual instruments combined are similar to Lumetrics Clearwave™ Plus, and the software is similar to Lumetrics OptiGauge Control Center v7.0 or higher. With the Clearwave™ Plus, a camera is used to find the lens edge, and then the lens center is calculated, which is then used to align a 1310 nanometer interferometer probe at the lens center for the measurement of sagittal height and center thickness. The transmitted wavefront is also collected in series using a wavefront sensor (shack-Hartmann sensor). Multiple parameters from the transmitted wavefront of the contact lens are measured, and others are calculated from those measurements.

From the data collected, difference terms are calculated by comparing the measured values from the target. These include root mean squared optical path wave front deviation from lens design target in μm (sphere/cylinder power and coma deviation removed) as measured using a 6.5 millimeter aperture (RMS_65), the second equivalent sphere power deviation from lens design target in diopters (D) as measured using a 5 millimeter aperture (PW2EQD), deviation from lens design target diameter in mm (DMD), deviation from lens design target base curve radius as calculated from the measured sagittal height and target lens diameter according to ISO 18369-3 in mm (BCD), and deviation from lens design target center thickness in mm (CTD). The amount of added spherical or cylindrical power created by the modulated and localized photopolymerization was calculated using such data after subtracting out the designed-in spherical power based on the mold design.

We claim:

1. A compound of formula I:

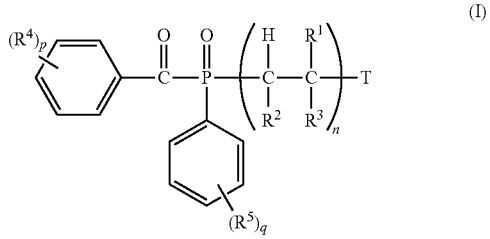

wherein $R^1$ at each occurrence is independently H or methyl;

$R^2$ and $R^3$ at each occurrence are independently H or —X'—N($R^6$)($R^7$), provided that at least one $R^2$ or $R^3$ is —X'—N($R^6$)($R^7$), wherein X' at each occurrence is independently a bond or —(CO)—, $R^6$ at each occurrence is independently H, $C_1$-$C_6$ alkyl, or $C_1$-$C_6$ alkylcarbonyl and $R^7$ at each occurrence is independently H, $C_1$-$C_6$ alkyl, or $C_1$-$C_6$ alkylcarbonyl, or $R^6$ and $R^7$ at any occurrence, together with the nitrogen atom to which they are bonded, form a heterocycloalkyl ring in which a ring carbon atom is optionally replaced with a heteroatom selected from nitrogen, oxygen, and sulfur, wherein each alkyl and alkylcarbonyl is independently optionally substituted with hydroxy, amino, amido, oxo, carboxy, alkyl carboxy, carbonyl, alkylcarbonyl, alkoxy, amido, carbamate, carbonate, halo, phenyl, or benzyl, and each heterocycloalkyl is independently optionally substituted with alkyl, hydroxy, amino, amido, oxo, carboxy, alkyl carboxy, carbonyl, alkylcarbonyl, alkoxy, amido, carbamate, carbonate, halo, phenyl, or benzyl;

$R^4$ and $R^5$, when present, are independently at each occurrence alkyl, cycloalkyl, alkoxy, or halo;

T is a chain termination group;

n is from 10 to 4000; and p and q are independently 0, 1, 2, 3, 4, or 5.

2. The compound of claim 1 wherein one of $R^2$ and $R^3$ at each occurrence is H.

3. The compound of claim 1 wherein q is 0.

4. The compound of claim 1 wherein p is 3 and $R^4$ at each occurrence is independently $C_1$-$C_3$ alkyl.

5. The compound of claim 1 wherein $R^6$ and $R^7$, together with the nitrogen atom to which they are bonded, form a heterocycloalkyl ring optionally substituted with alkyl, hydroxy, amino, amido, oxo, carboxy, alkyl carboxy, carbonyl, alkylcarbonyl, alkoxy, amido, carbamate, carbonate, or halo.

6. The compound of claim 1 wherein $R^6$ and $R^7$, together with the nitrogen atom to which they are bonded, form imidazolidinyl, piperazinyl, pyrrolidinyl, or piperidinyl optionally substituted with alkyl or oxo.

7. The compound of claim 1 wherein $R^6$ and $R^7$, together with the nitrogen atom to which they are bonded, form 2-pyrrolidinone.

8. The compound of claim 1 wherein $R^6$ and $R^7$ are independently H, $C_1$-$C_6$ alkyl, or $C_1$-$C_6$ alkylcarbonyl, wherein alkyl and alkylcarbonyl are independently optionally substituted with hydroxy.

9. The compound of claim 1 wherein $R^6$ and $R^7$ are independently H or $C_1$-$C_4$ alkyl, wherein alkyl is optionally substituted with hydroxy.

10. The compound of claim 1 wherein $R^6$ and $R^7$ are both H.

11. The compound of claim 1 wherein $R^6$ is H and $R^7$ is $C_1$-$C_3$ alkyl or $C_1$-$C_3$ alkylcarbonyl, wherein alkyl is optionally substituted with hydroxy.

12. The compound of claim 1 wherein $R^6$ and $R^7$ are independently $C_1$-$C_3$ alkyl optionally substituted with hydroxy.

13. The compound of claim 1 wherein $R^6$ is $C_1$-$C_3$ alkyl optionally substituted with hydroxy and $R^7$ is $C_1$-$C_3$ alkylcarbonyl.

14. The compound of claim 1 wherein X' is —(CO)—.

15. The compound of claim 1 wherein X' is a direct bond.

16. The compound of claim 1 that is:

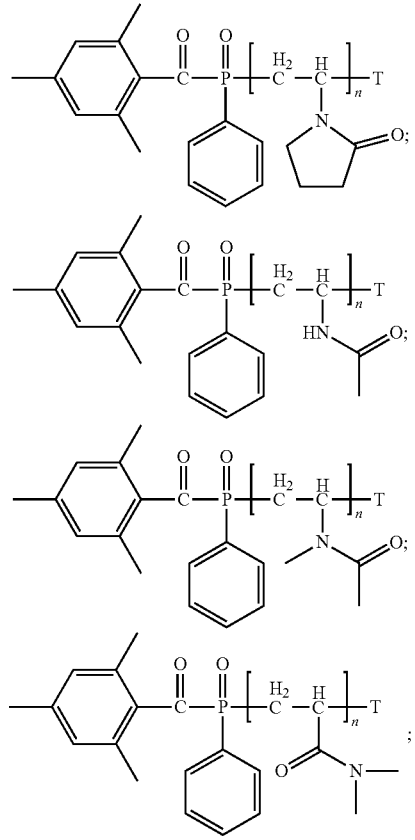

-continued

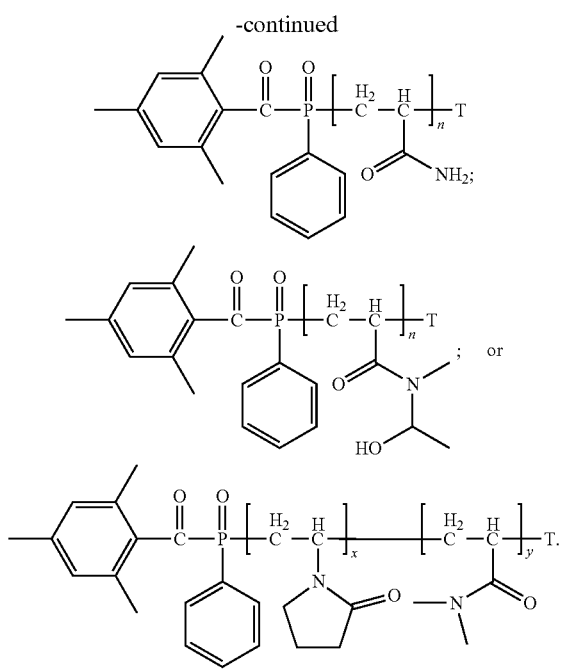

17. A method for forming an ophthalmic lens, the method comprising:
(a) providing a mold assembly comprised of a base curve and a front curve, the base curve and the front curve defining and enclosing a cavity therebetween, the cavity containing a reactive monomer mixture, wherein the reactive monomer mixture comprises a monomer suitable for making the ophthalmic lens, a first polymerization initiator that is capable of being activated at a first wavelength, a first functional moiety chemically linked to the first polymerization initiator, and a second polymerization initiator that is capable of being activated by a second activation that does not substantially activate the first polymerization initiator, wherein at least one of the base curve or front curve is light transmissive;
(b) exposing one or more selective regions of the reactive monomer mixture to a source of actinic radiation at the first wavelength to thereby selectively polymerize a portion of the reactive monomer mixture, wherein the selectively polymerized portion incorporates the first functional moiety;
(c) exposing the reactive monomer mixture to the second activation to activate the second polymerization initiator and cure the reactive monomer mixture;
(d) removing the ophthalmic lens from the mold assembly; and
(e) extracting unreacted first polymerization initiator from the ophthalmic lens, wherein the first polymerization initiator having a chemically linked first functional moiety is a compound of claim 1.

18. A reactive monomer mixture for making an ophthalmic lens, the reactive monomer mixture comprising:
a monomer suitable for making the ophthalmic lens;
a first polymerization initiator capable of being activated at a first wavelength;
a first functional moiety chemically linked to the first polymerization initiator; and
a second polymerization initiator that is capable of being activated by a second activation that does not substantially activate the first polymerization initiator,
wherein the first polymerization initiator having a chemically linked first functional moiety is a compound of claim 1.

* * * * *